US005786212A

United States Patent [19]

James et al.

[11] Patent Number: 5,786,212

[45] Date of Patent: Jul. 28, 1998

[54] MULTIPLE INTEGRATIVE VECTORS AND YARROWIA LIPOLYTICA TRANSFORMANTS

[75] Inventors: Larry C. James, Norwich; Christine A. Strick, Lisbon, both of Conn.

[73] Assignee: Pfizer Inc., New York, N.Y.

[21] Appl. No.: 596,382

[22] PCT Filed: May 30, 1994

[86] PCT No.: PCT/IB94/00128

§ 371 Date: May 6, 1996

§ 102(e) Date: May 6, 1996

[87] PCT Pub. No.: WO95/06739

PCT Pub. Date: Mar. 9, 1995

Related U.S. Application Data

[63] Continuation of Ser. No. 117,375, Sep. 2, 1993, abandoned.

[51] Int. Cl.[6] .......................... C12N 15/81; C12N 15/11; C12P 21/02; C07H 21/04
[52] U.S. Cl. ................... 435/320.1; 435/69.1; 435/91.1; 435/172.3; 435/252.8; 435/254.11; 536/23.1; 536/24.1
[58] Field of Search ........................ 536/24.1, 23.1; 435/91.1, 254.11, 252.8, 69.1, 172.3, 320.1

[56] References Cited

FOREIGN PATENT DOCUMENTS

| 0 220 864 | 5/1987 | European Pat. Off. . |
| 0329501 | 8/1989 | European Pat. Off. . |

OTHER PUBLICATIONS

Gaillardin et al. "Leu 2 Directed Expression of Beta–Galactosidase Activity and Phleomycin Resistance in *Yarrowia lipolytica*" Current Genetics 11(5) 369–375, 1987.

Matsuoka et al "Analysis of Regions Essential for the Function of Chromosomal Replicator Sequences from *Yarrowia lipolytica*" Mol. Gen Genet. 237 327–333, 1993.

Primary Examiner—Nancy Degen
Attorney, Agent, or Firm—Peter C. Richardson; Gregg C. Benson; Robert F. Sheyka

[57] ABSTRACT

This invention relates to modified *Yarrowia lipolytica* LEU2 gene promoters; modified *Y. lipolytica* LEU2 genes comprising such modified *Y. lipolytica* LEU2 gene promoters; and vectors comprising such modified *Y. lipolytica* LEU2 genes. This invention also relates to vectors comprising a *Y. lipolytica* DNA sequence LEU2 genes. This invention also relates to vectors comprising a *Y. lipolytica* DNA sequence sufficient for integrative transformation of *Y. lipolytica*; vectors which comprise a nucleotide sequence coding for a polypeptide and a promoter functional in *Y. lipolytica* operably linked thereto; *E. coli* transformants which comprise vectors according to this invention; *Y. lipolytica* transormants which comprise an expression vector according to this invention; methods of producing *Y. lipolytica* transformants comprising multiple integrated expression vectors; strains of *Y. lipolytica* useful in the preparation of such transformants; methods of producing polypeptides with certain of the *Y. lipolytica* transformants; nucleotide sequences useful in the preparation of modified *Y. lipolytica* LEU2 gene promoters according to this invention and a method for producing modified *Y. lipolytica* LEU2 promoters.

47 Claims, 18 Drawing Sheets

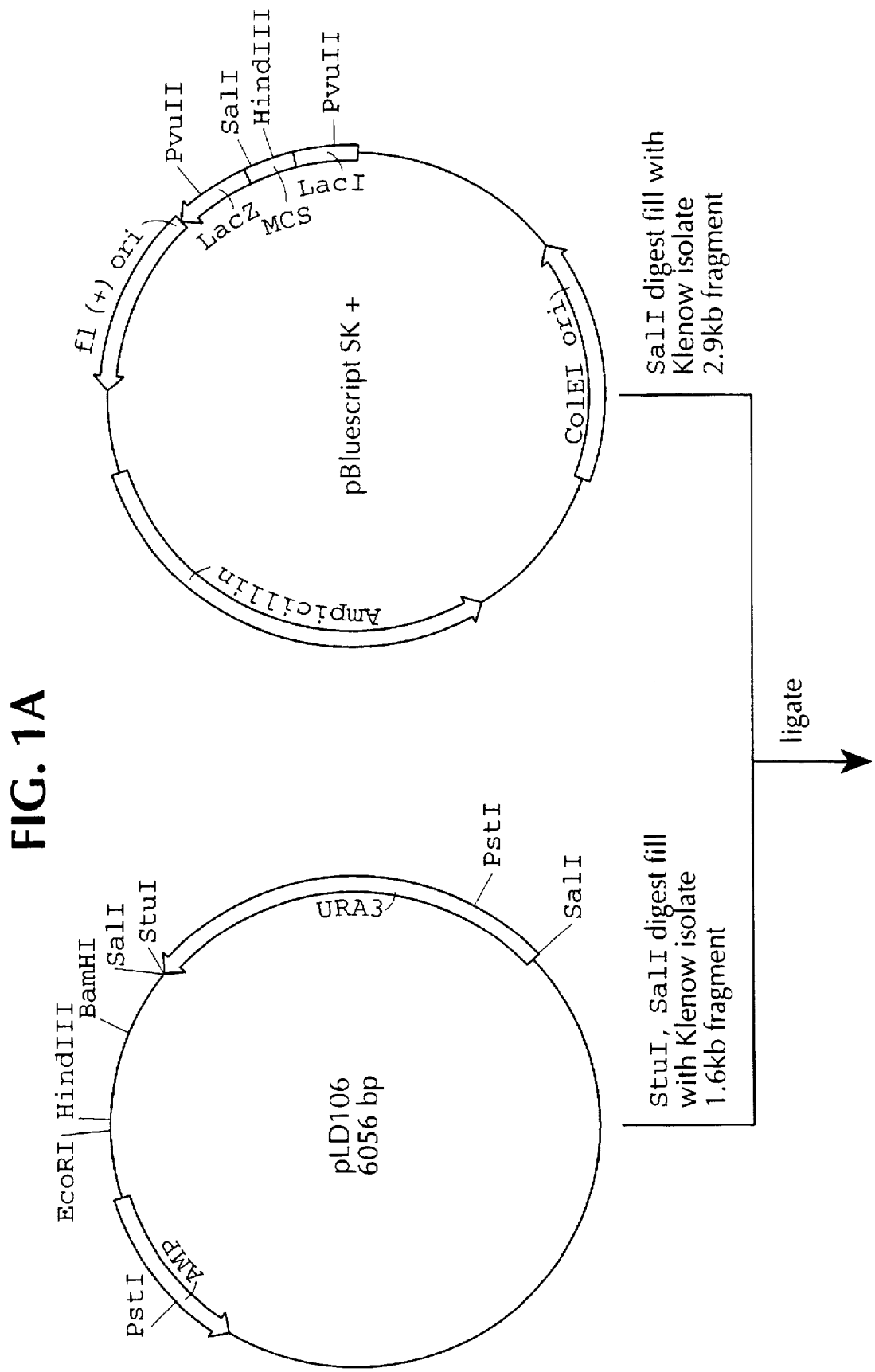

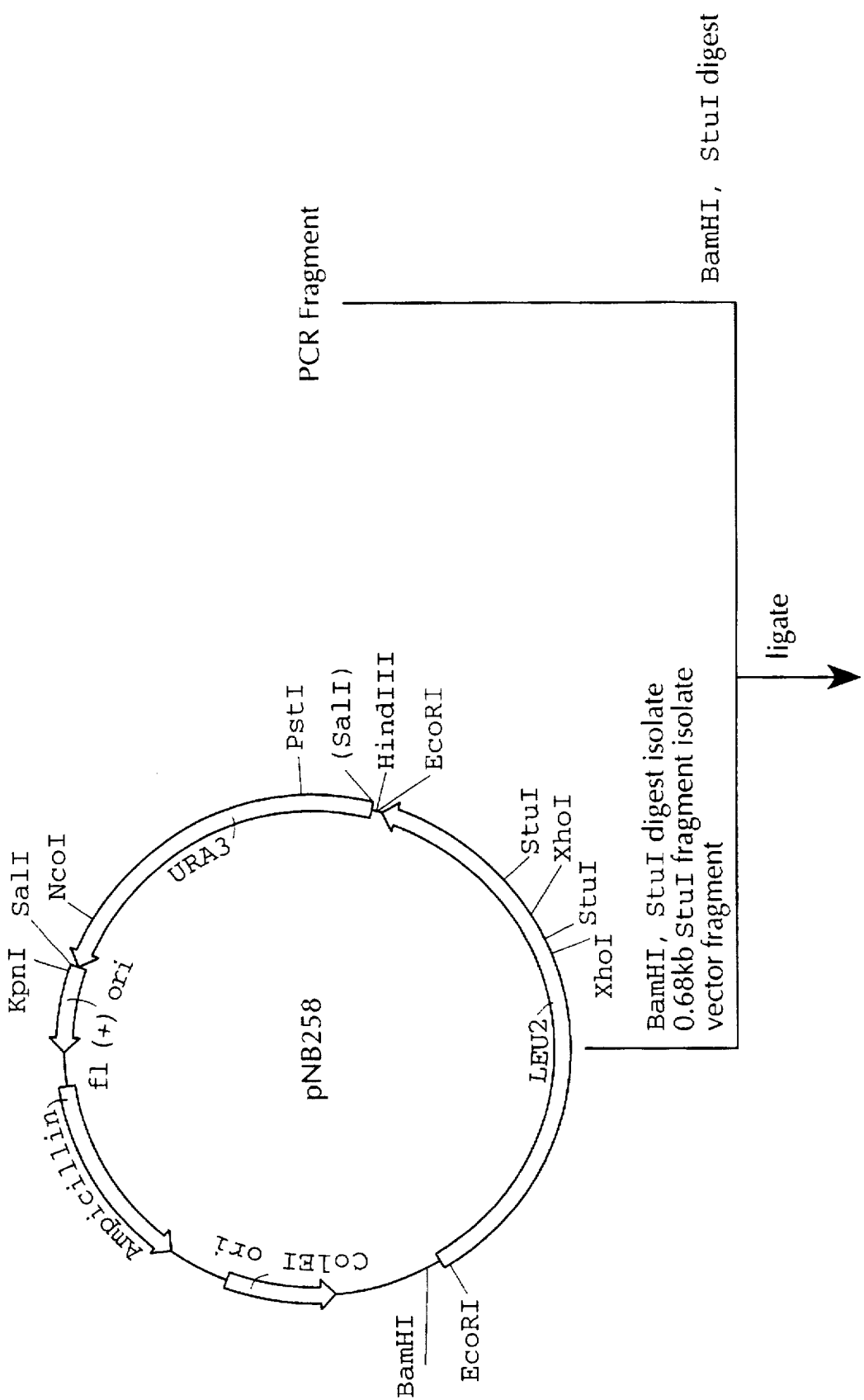

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 2810 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

```
GTCGACACCA  TATCATATAA  AACTAACAAT  GCATTGCTTA  TTACGAAGAC  TACCCGTTGC   60

TATCTCCACA  CCGTTATCTC  CACGGTCCAA  AGGCTGCTCA  ATGTGCTGCA  TACGTAACGT  120

GGGGTGCAAC  CTTGAGCACA  TAGTACTTTT  CCGAAAACCG  GCGATAATTA  AGTGTGCACT  180

CCAACTTTTC  ACACTGAGCG  TAAAATGTGG  AGAAGAAATC  GGCACTAAAA  AGTCAGGTAG  240

ACTGGAAAAT  GCGCCATGAA  ATGAATATCT  CTTGCTACAG  TAATGCCCAG  CATCGAGGGG  300

TATTGTGTCA  CCAACACTAT  AGTGGCAGCT  GAAGCGCTCG  TGATTGTAGT  ATGAGTCTTT  360

ATTGGTGATG  GGAAGAGTTC  ACTCAATATT  CTCGTTACTG  CCAAAACACC  ACGGTAATCG  420

GCCAGACACC  ATGGATGTAG  ATCACCAAGC  CTGTGAATGT  TATTCGAGCT  AAAATGCACA  480

TGGTTGGTGA  AAGGAGTAGT  TGCTGTCGAA  TTCCGTCGTC  GCCTGAGTCA  TCATTTATTT  540

ACCAGTTGGC  CACAAACCCT  TGACGATCTC  GTATGTCCCC  TCCGACATAC  TCCCGGCCGG  600
```

| | | | | | |
|---|---|---|---|---|---|
| CTGGGGTACG | TTCGATAGCG | CTATCGGCAT | CGACAAGGTT | TGGGTCCCTA | GCCGATACCG | 660 |
| CACTACCTGA | GTCACAATCT | TCGGAGGTTT | AGTCTTCCAC | ATAGCACGGG | CAAAAGTGCG | 720 |
| TATATATACA | AGAGCGTTTG | CCAGCCACAG | ATTTTCACTC | CACACACCAC | ATCACACATA | 780 |
| CAACCACACA | CATCCACAAT | GGAACCCGAA | ACTAAGAAGA | CCAAGACTGA | CTCCAAGAAG | 840 |
| ATTGTTCTTC | TCGGCGGCGA | CTTCTGTGGC | CCCGAGGTGA | TTGCCGAGGC | CGTCAAGGTG | 900 |
| CTCAAGTCTG | TTGCTGAGGC | CTCCGGCACC | GAGTTTGTGT | TGAGGACCG | ACTCATTGGA | 960 |
| GGAGCTGCCA | TTGAGAAGGA | GGGCGAGCCC | ATCACCGACG | CTACTCTCGA | CATCTGCCGA | 1020 |
| AAGGCTGACT | CTATTATGCT | CGGTGCTGTC | GGAGGCGCTG | CCAACACCGT | ATGGACCACT | 1080 |
| CCCGACGGAC | GAACCGACGT | GCGACCCGAG | CAGGGTCTCC | TCAAGCTGCG | AAAGGACCTG | 1140 |
| AACCTGTACG | CCAACCTGCG | ACCCTGCCAG | CTGCTGTCGC | CCAAGCTCGC | CGATCTCTCC | 1200 |
| CCCATCCGAA | ACGTTGAGGG | CACCGACTTC | ATCATTGTCC | GAGAGCTCGT | CGGAGGTATC | 1260 |
| TACTTTGGAG | AGCGAAAGGA | GGATGACGGA | TCTGGCGTCG | CTTCCGACAC | CGAGACCTAC | 1320 |
| TCCGTTCCTG | AGGTTGAGCG | AATTGCCCGA | ATGGCCGCCT | TCCTGGCCCT | TCAGCACAAC | 1380 |
| CCCCCTCTTC | CCGTGTGGTC | TCTTGACAAG | GCCAACGTGC | TGGCCTCCTC | TCGACTTTGG | 1440 |
| CGAAAGACTG | TCACTCGAGT | CCTCAAGGAC | GAATTCCCCC | AGCTCGAGCT | CAACCACCAG | 1500 |
| CTGATCGACT | CGGCCGCCAT | GATCCTCATC | AAGCAGCCCT | CCAAGATGAA | TGGTATCATC | 1560 |
| ATCACCACCA | ACATGTTTGG | CGATATCATC | TCCGACGAGG | CCTCCGTCAT | CCCCGGTTCT | 1620 |
| CTGGGTCTGC | TGCCCTCCGC | CTCTCTGGCT | TCTCTGCCCG | ACACCAACGA | GGCGTTCGGT | 1680 |
| CTGTACGAGC | CCTGTCACGG | ATCTGCCCCC | GATCTCGGCA | AGCAGAAGGT | CAACCCCATT | 1740 |
| GCCACCATTC | TGTCTGCCGC | CATGATGCTC | AAGTTCTCTC | TTAACATGAA | GCCCGCCGGT | 1800 |
| GACGCTGTTG | AGGCTGCCGT | CAAGGAGTCC | GTCGAGGCTG | GTATCACTAC | CGCCGATATC | 1860 |
| GGAGGCTCTT | CCTCCACCTC | CGAGGTCGGA | GACTTGTTGC | CAACAAGGTC | AAGGAGCTGC | 1920 |
| TCAAGAAGGA | GTAAGTCGTT | TCTACGACGC | ATTGATGGAA | GGAGCAAACT | GACGCGCCTG | 1980 |
| CGGGTTGGTC | TACCGGCAGG | GTCCGCTAGT | GTATAAGACT | CTATAAAAAG | GGCCCTGCCC | 2040 |
| TGCTAATGAA | ATGATGATTT | ATAATTTACC | GGTGTAGCAA | CCTTGACTAG | AAGAAGCAGA | 2100 |
| TTGGGTGTGT | TTGTAGTGGA | GGACAGTGGT | ACGTTTGGA | AACAGTCTTC | TTGAAAGTGT | 2160 |
| CTTGTCTACA | GTATATTCAC | TCATAACCTC | AATAGCCAAG | GGTGTAGTCG | GTTATTAAA | 2220 |
| GGAAGGGAGT | TGTGGCTGAT | GTGGATAGAT | ATCTTTAAGC | TGGCGACTGC | ACCCAACGAG | 2280 |
| TGTGGTGGTA | GCTTGTTACT | GTATATTCGG | TAAGATATAT | TTTGTGGGGT | TTTAGTGGTG | 2340 |
| TTTGGTAGGT | TAGTGCTTGG | TATATGAGTT | GTAGGCATGA | CAATTTGGAA | AGGGGTGGAC | 2400 |
| TTTGGGAATA | TTGTGGGATT | TCAATACCTT | AGTTTGTACA | GGGTAATTGT | TACAAATGAT | 2460 |
| ACAAAGAACT | GTATTTCTTT | TCATTTGTTT | TAATTGGTTG | TATATCAAGT | CCGTTAGACG | 2520 |
| AGCTCAGTGC | CATGGCTTTT | GGCACTGTAT | TTCATTTTTA | GAGGTACACT | ACATTCAGTG | 2580 |
| AGGTATGGTA | AGGTTGAGGG | CATAATGAAG | GCACCTTGTA | CTGACAGTCA | CAGACCTCTC | 2640 |
| ACCGAGAATT | TTATGAGATA | TACTCGGGTT | CATTTTAGGC | TCCGATTCGA | TTCAAATTAT | 2700 |
| TACTGTCGAA | ATCGGTTGAG | CATCCGTTGA | TTTCCGAACA | GATCTCGGCA | GTCTCTCGGA | 2760 |
| TGTAGAATTA | GGTTTCCTTG | AGGCGAAGAT | CGGTTTGTGT | GACATGAATT | | 2810 |

( 2 ) INFORMATION FOR SEQ ID NO:2:

( i ) SEQUENCE CHARACTERISTICS:
      ( A ) LENGTH: 29 base pairs
      ( B ) TYPE: nucleic acid (C) STRANDEDNESS: single
        (D) TOPOLOGY: linear (ii) MOLECULE TYPE: cDNA (xi) SEQUENCE DESCRIPTION: SEQ ID NO:2:

TCGAGTCCTC AAGGACGAAT TTCCCCAGC                                              29

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TCGAGCTGGG GAAATTCGTC CTTGAGGAC                                              29

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GCAGGATCCG AATTCCTTGA CGATCTCGTA TGTC                                        34

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GCAGGATCCG AATTCGCTGG GGTACGTTCG ATAG                                        34

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCAGGATCCG AATTCTAGCC GATACCGCAC TACC                                        34

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA ( x i ) SEQUENCE DESCRIPTION: SEQ ID NO:7:

GCAGGATCCG AATTCTCTTC CACATAGCAC GGGC                34

( 2 ) INFORMATION FOR SEQ ID NO:8:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GCAGGATCCG AATTCCGTAT ATATACAAGA GCGTTTGCC            39

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GCAGGATCCG AATTCCGTAT GTATACAAGA GCGTTTGCC            39

( 2 ) INFORMATION FOR SEQ ID NO:10:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GCAGGATCCG AATTCCGTAT AGATACAAGA GCGTTTGCC            39

( 2 ) INFORMATION FOR SEQ ID NO:11:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GCAGGATCCG AATTCCGTGT ATATACAAGA GCGTTTGCC            39

( 2 ) INFORMATION FOR SEQ ID NO:12:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GCAGGATCCG AATTCCCACA GATTTCACT CC                    32

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

```
CACAAACTCG GTGCCGGAGG CC                                             22
```

( 2 ) INFORMATION FOR SEQ ID NO:14:

( i ) SEQUENCE CHARACTERISTICS:
        ( A ) LENGTH: 279 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

```
ATTCTTTGTG AACCAACACC TGTGCGGATC CCACCTGGTG GAAGCTCTCC ACCTAGTGTG    60
CGGGGAACGA GGCTTCTTCT ACACACCCAA GACCCGCCGG AGGGCAGAGG ACCTGCAGGT   120
GGGGCAGGTG GAGCTGGGCG GGGGCCCTGG TGCAGGCAGC CTGCAGCCCT TGGCCCTGGA   180
GGGGTCCCTG CAGAAGCGTG GCATTGTGGA ACAATGCTGT ACCAGCATCT GCTCCCTCTA   240
CCAGCTGGAG AACTACTGCA ACTAGAAGCT TGGCCGCGG                         279
```

( 2 ) INFORMATION FOR SEQ ID NO:15:

( i ) SEQUENCE CHARACTERISTICS:
        ( A ) LENGTH: 271 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

```
GGCCAAGCTT CTAGTTGCAG TAGTTCTCCA GCTGGTAGAG GGAGCAGATG CTGGTACAGC    60
ATTGTTCCAC AATGCCACGC TTCTGCAGGG ACCCCTCCAG GGCCAAGGGC TGCAGGCTGC   120
CTGCACCAGG GCCCCGCCC AGCTCCACCT GCCCCACCTG CAGGTCCTCT GCCCTCCGGC   180
GGGTCTTGGG TGTGTAGAAG AAGCCTCGTT CCCCGCACAC TAGGTGGAGA GCTTCCACCA   240
GGTGGGATCC GCACAGGTGT TGGTTCACAA A                                  271
```

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

```
TACACGGATG GATCTGG                                                   17
```

( 2 ) INFORMATION FOR SEQ ID NO:17:

( i ) SEQUENCE CHARACTERISTICS:
        ( A ) LENGTH: 35 base pairs

-continued ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

CACGCCGAGG GCACCTTCAC CTCCGACGTC TCCTC                                    35

( 2 ) INFORMATION FOR SEQ ID NO:18:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CCGGGTGCGG CTCCCGTGGA AGTGGAGGCT GCAGAGGAGG ATGG                          44

( 2 ) INFORMATION FOR SEQ ID NO:19:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

CTACCTGGAG GGACAGGCCG CCAAGGAGTT CATCGCCTGG CTGGTCAAGG GACGAGGATA         60

GT                                                                        62

( 2 ) INFORMATION FOR SEQ ID NO:20:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

ACCTCCCTGT CCGGCGGTTC CTCAAGTAGC GGACCGACCA GTTCCCTGCT CCTATCAGAT         60

C                                                                         61

1

MULTIPLE INTEGRATIVE VECTORS AND *YARROWIA LIPOLYTICA* TRANSFORMANTS

This is a 371 of PCT/IB94/00128 which is a continuation of U.S. patent application Ser. No. 08/117,375 filed Sep. 2, 1993, now abandoned.

TECHNICAL FIELD

This invention relates to modified *Yarrowia lipolytica* LEU2 gene promoters and to modified *Y. lipolytica* LEU2 genes comprising such modified *Y. lipolytica* LEU2 gene promoters. This invention further relates to vectors comprising such modified *Y. lipolytica* LEU2 genes. Such vectors include vectors comprising a *Y. lipolytica* DNA sequence sufficient for integrative transformation of *Y. lipolytica* at a locus other that the LEU2 locus of *Y. lipolytica*; and vectors which comprise a nucleotide sequence coding for a polypeptide and a promoter functional in *Y. lipolytica* operably linked thereto. The latter vectors are also known as expression vectors. Further still, this invention relates to *E. coli* transformants comprising vectors of this invention.

This invention also relates to *Y. lipolytica* transformants which comprise an expression vector according to this invention; to methods of producing *Y. lipolytica* transformants comprising multiple integrated expression vectors; to strains of *Y. lipolytica* useful in the preparation of such transformants; and to methods of producing polypeptides with certain of the *Y. lipolytica* transformants. Further still, this invention relates to nucleotide sequences useful in the preparation of modified *Y. lipolytica* LEU2 gene promoters according to this invention and a method for producing modified *Y. lipolytica* LEU2 promoters.

BACKGROUND ART

Processes for transformation of *Y. lipolytica* as well as vectors useful therefor and transformants comprising such vectors, inter alia, are disclosed and claimed in U.S. Pat. Nos. 4,880,741 and 5,071,764, both of which are assigned to the assignee hereof. Vectors useful in transformation of *Y. lipolytica* for expression and secretion of heterologous proteins as well as transformants and processes for producing heterologous protein therewith, inter alia, are disclosed and claimed in U.S. Pat. No. 4,937,189 which also is assigned to the assignee hereof. U.S. Pat. No. 4,937,189 also discloses the nucleotide sequence of the LEU2 gene of *Y. lipolytica* (SEQUENCE I.D. NO: 1).

WO91/00920 (PCT/EP90/01138), published Jan. 24, 1991, discloses a process for preparing a homologous or heterologous protein by a yeast transformed by multicopy integration of an expression vector into the genome of the yeast. The expression vector used in that process contains both an "expressible gene" encoding the desired protein and a "deficient selection marker needed for the growth of the yeast in a specific medium" such as a defective LEU2 gene (leu2d). Also disclosed are such vectors which also contain DNA coding for ribosomal RNA.

WO92/01800 (PCT/US91/04899), published Feb. 6, 1992, discloses integrating plasmid vectors capable of inserting throughout the yeast genome with high copy number and a process to accomplish such integration. The vectors disclosed use "dispersed repetitive elements (DRE's)" such as the yeast DELTA sequences, Ty sequences and tRNA DNA sequences.

DISCLOSURE OF THE INVENTION

This invention provides modified *Y. lipolytica* LEU2 gene promoters useful in the preparation of modified *Y. lipolytica* LEU2 genes. More specifically, this invention provides modified *Y. lipolytica* LEU2 gene promoters selected from the group consisting of nucleotides 693 to 798 of SEQUENCE I.D. NO: 1, nucleotides 718 to 798 of SEQUENCE I.D. NO: 1, nucleotides 718 to 798 of SEQUENCE I.D. NO: 1 wherein nucleotide 724 is changed from A to G, nucleotides 718 to 798 of SEQUENCE I.D. NO: 1 wherein nucleotide 725 is changed from T to G, nucleotides 718 to 798 of SEQUENCE I.D. NO: 1 wherein nucleotide 722 is changed from A to G, nucleotides 745 to 798 of SEQUENCE I.D. NO: 1, and the functional equivalents thereof. This invention also provides modified *Y. lipolytica* LEU2 genes comprising a modified LEU2 gene promoter according to this invention functionally linked to a *Y. lipolytica* LEU2 structural gene coding sequence.

This invention further provides vectors comprising modified *Y. lipolytica* LEU2 genes as described hereinabove. Still further, this invention provides vectors comprising a modified *Y. lipolytica* LEU2 gene as described hereinabove and a *Y. lipolytica* DNA sequence sufficient for integrative transformation of *Y. lipolytica* at a locus other than the LEU2 locus of *Y. lipolytica*. A preferred *Y. lipolytica* DNA sequence for such vectors is a *Y. lipolytica* ribosomal DNA sequence. Also provided by this invention is a vector which is useful in the construction of expression vectors as described hereinbelow.

The vectors according to this invention comprising a *Y. lipolytica* DNA sequence sufficient for integrative transformation at a locus other than the LEU2 locus are capable, upon transformation, of integrating at multiple sites and, hence, result in *Y. lipolytica* transformants comprising multiple copies of such vectors.

The invention further provides expression vectors which, upon transformation of *Y. lipolytica*, result in both expression of a heterologous polypeptide and secretion thereof by said *Y. lipolytica*. Such expression vectors comprise a modified *Y. lipolytica* LEU2 gene (as described hereinabove), a DNA sequence sufficient for integrative transformation of *Y. lipolytica* at a locus other than the LEU2 locus of *Y. lipolytica*, an XPR2 promoter of *Y. lipolytica* and, operably linked to such a promoter, the signal, pro-1 or pro-2 sequence of the XPR2 gene of *Y. lipolytica*, or a functional fragment or equivalent thereof, which, in turn, is operably linked to a coding sequence for a polypeptide. Preferred are such expression vectors comprising the signal, pro-1 or pro-2 sequence of the XPR2 gene of *Y. lipolytica* wherein the DNA sequence sufficient for integrative transformation of *Y. lipolytica* at a locus other than the LEU2 locus is a *Y. lipolytica* ribosomal DNA sequence. Also preferred are such expression vectors or preferred expression vectors wherein the polypeptide is a heterologous polypeptide. Preferred heterologous polypeptides of this invention include prochymosin, proinsulin analog, insulinotropin and human TGF-β3.

Still further, this invention provides *Y. lipolytica* transformants comprising the expression vectors of this invention. Also provided by this invention is a *Y. lipolytica* strain comprising a deletion in the LEU2 locus which strain is useful in the selection of modified LEU2 genes according to this invention and *E. coli* transformants comprising vectors of this invention.

Yet further still, this invention provides processes for producing a polypeptide which comprise fermenting a *Y. lipolytica* transformant of this invention in an aqueous nutrient medium comprising assimilable sources of carbon, nitrogen and inorganic salts.

Also provided by this invention is a method of producing *Y. lipolytica* transformants comprising multiple integrated expression vectors. The method comprises transforming a *Y. lipolytica* strain having a deletion of the LEU2 gene thereof with an expression vector capable of integrative transformation as described hereinabove and which vector has been linearized by cleaving the expression vector in the DNA sequence sufficient for integrative transformation, and selecting the best growing transformants on a medium which lacks leucine.

A method of producing a modified *Y. lipolytica* LEU2 promoter is also provided by this invention. The method comprises producing a DNA sequence having a 5' end and a 3' end, having homology or substantial homology to a region of SEQUENCE I.D. NO: 1 and wherein said 5' end is within, but not co-terminus with the 5' end of the promoter region of SEQUENCE I.D. NO: 1; producing a vector comprising (i) a DNA sequence wherein the 3' end of the DNA sequence produced as described immediately above is joined to the 5' end of a DNA sequence comprising nucleotides from SEQUENCE I.D. NO: 1 such that the structural gene for LEU2 is formed and (ii) a sequence coding for a second *Y. lipolytica* structural gene; transforming a *Y. lipolytica* host having a deletion of the LEU2 gene and a mutation or deletion in the structural gene corresponding to said second structural gene with the vector produced as described immediately above, which vector has been cleaved within the region coding for said second structural gene; selecting *Y. lipolytica* transformants on a medium containing leucine but requiring said second structural gene for growth; and screening such transformants for a transformant which grows poorly on a medium lacking leucine. A preferred second structural gene for use in the above method is the URA3 gene of *Y. lipolytica*.

As used throughout this Specification and the appendant claims, "functional fragment" means a fragment of the sequence to which the phrase refers which fragment has a function which is at least part of the overall function of the complete sequence.

As used throughout this Specification and the appendant claims, "functional equivalent" means a sequence having the same, or substantially the same function as the sequence to which the phrase refers.

BRIEF DESCRIPTION OF THE DRAWINGS

FIGS. 1A–1D are schematic representations of the construction of plasmid pNB276.

MATERIALS AND METHODS

Figure 1B:
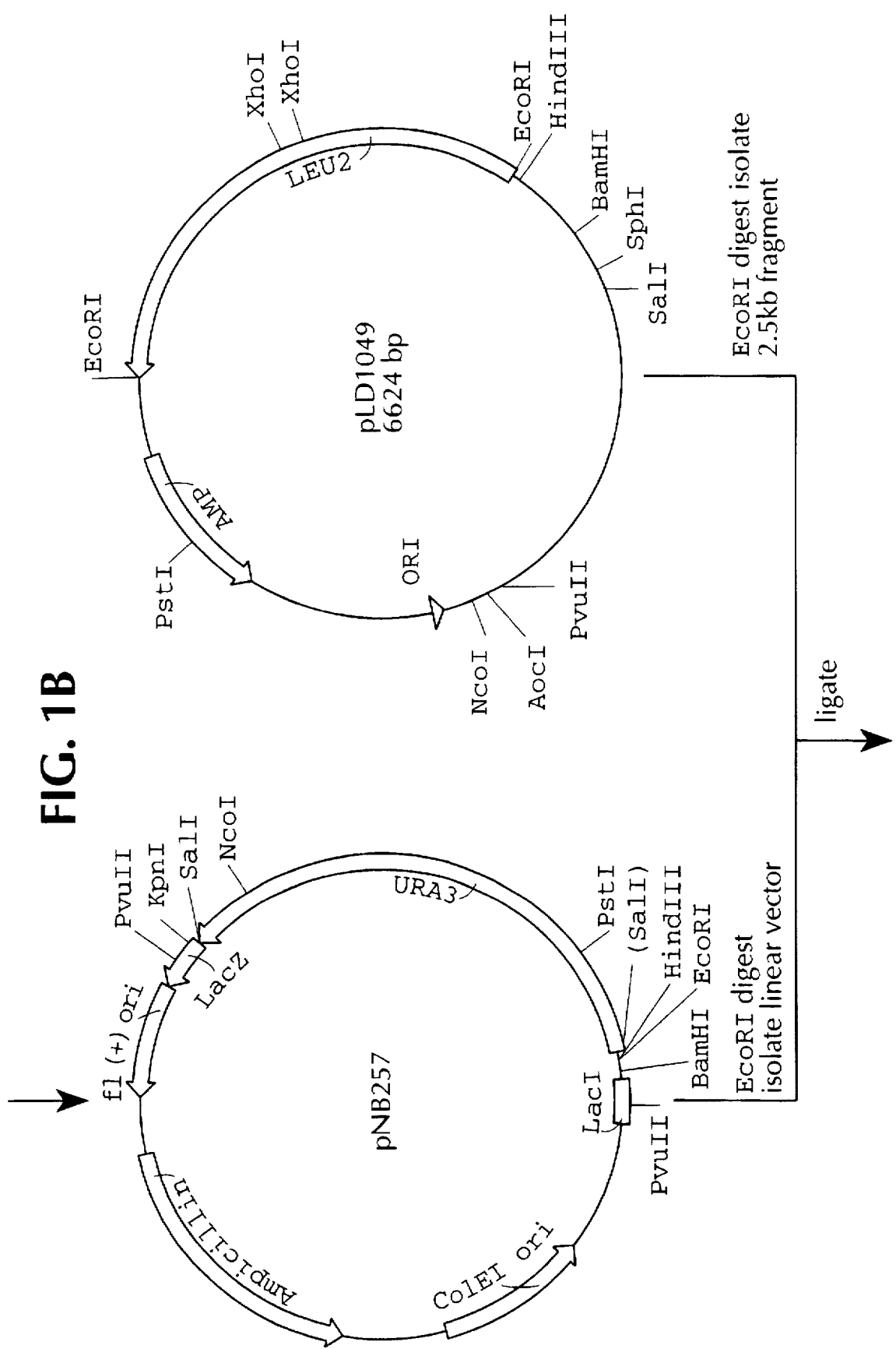

*E. coli* strain DH5α (obtained as competent cells from Bethesda Research Laboratories, Gaithersburg, Md.) was used as host for plasmid preparation. *E. coli* cells were transformed according to the supplier's recommended procedure and grown on LB medium plus ampicillin (100 µg/ml) at 37° C. LB medium contained (per liter): 10 g Bactotryptone, 5 g Bacto yeast extract and 10 g sodium chloride. Plasmid DNA was prepared using the alkaline lysis method (Birnboim, H. C. et al., NAR 7, 1513 (1979) or the boiling method (Holmes, D. S. et al., Anal. Biochem. 114:193 (1981)).

Restriction endonucleases, T4 polymerase, T4 DNA ligase, Klenow DNA polymerase, calf intestinal alkaline phosphatase, as well other necessary enzymes as indicated hereinbelow were purchased from New England Biolabs (Beverly, Mass.) and/or Bethesda Research Laboratories (Gaithersburg, Md.) and were used according to the supplier's recommended conditions. All molecular biological manipulations were performed according to standard methods (Sambrook, J., E. F. Fritsch and T. Maniatis, *Molecular Cloning, A Laboratory Manual* (2nd Ed.) CSHL Press (1989)).

*Y. lipolytica* strains were grown on standard rich yeast medium (YPD) containing 1% Bacto-yeast extract, 2% Bacto-peptone and 2% dextrose, or on complete minimal medium without leucine (Sherman, F., et al., *Laboratory Course Manual for Methods in Yeast Genetics*, CSHL Press 1986) at 28° C. Transformation was performed as described by Davidow, L. S., et al., Curr Genet 10: 39–48 (1985). For expression, cultures were grown on Medium A (5% Bacto-peptone, 1% glucose, 0.1% yeast extract). Yeast DNA was prepared as described by Sherman, F., et al., *Laboratory Course Manual for Methods in Yeast Genetics*, CSHL Press (1986) and Southern analysis was performed using standard conditions (Sambrook, J., E. F. Fritsch and T. Maniatis, *Molecular Cloning, A Laboratory Manual* (2nd Ed.) CSHL Press 1989). The methods referenced above are well known to those skilled in the art.

DETAILED DESCRIPTION

1. CONSTRUCTION OF MODIFIED *Y. lipolytica* LEU2 GENE PROMOTERS AND MODIFIED *Y. lipolytica* LEU2 GENES.

The nucleotide sequence of the *Y. lipolytica* LEU2 gene is given in the Sequence Listing, below, as SEQUENCE I.D. NO: 1. The *Y. lipolytica* LEU2 gene nucleotide sequence is disclosed, inter alia, in U.S. Pat. No. 4,937,189, which is assigned to the assignee hereof and which is incorporated herein by reference. Further, plasmid pLD25 containing the *Y. lipolytica* LEU2 gene is disclosed in U.S. Pat. No. 5,071,764, and disclosed and claimed in U.S. Pat. No. 4,880,741, both of which are also assigned to the assignee hereof and which are incorporated herein by reference. Plasmid pLD25 has been deposited with the American Type Culture Collection, Rockville, Md., USA under the terms of the Budapest Treaty in the form of an *E. coli* transformant (*E. coli* JC-355 transformant with pLD25) and has been designated ATCC 39464. All restrictions on availability of ATCC 39464 have been irrevocably removed by virtue of the grant of U.S. Pat. No. 4,880,741.

Figure 1D:
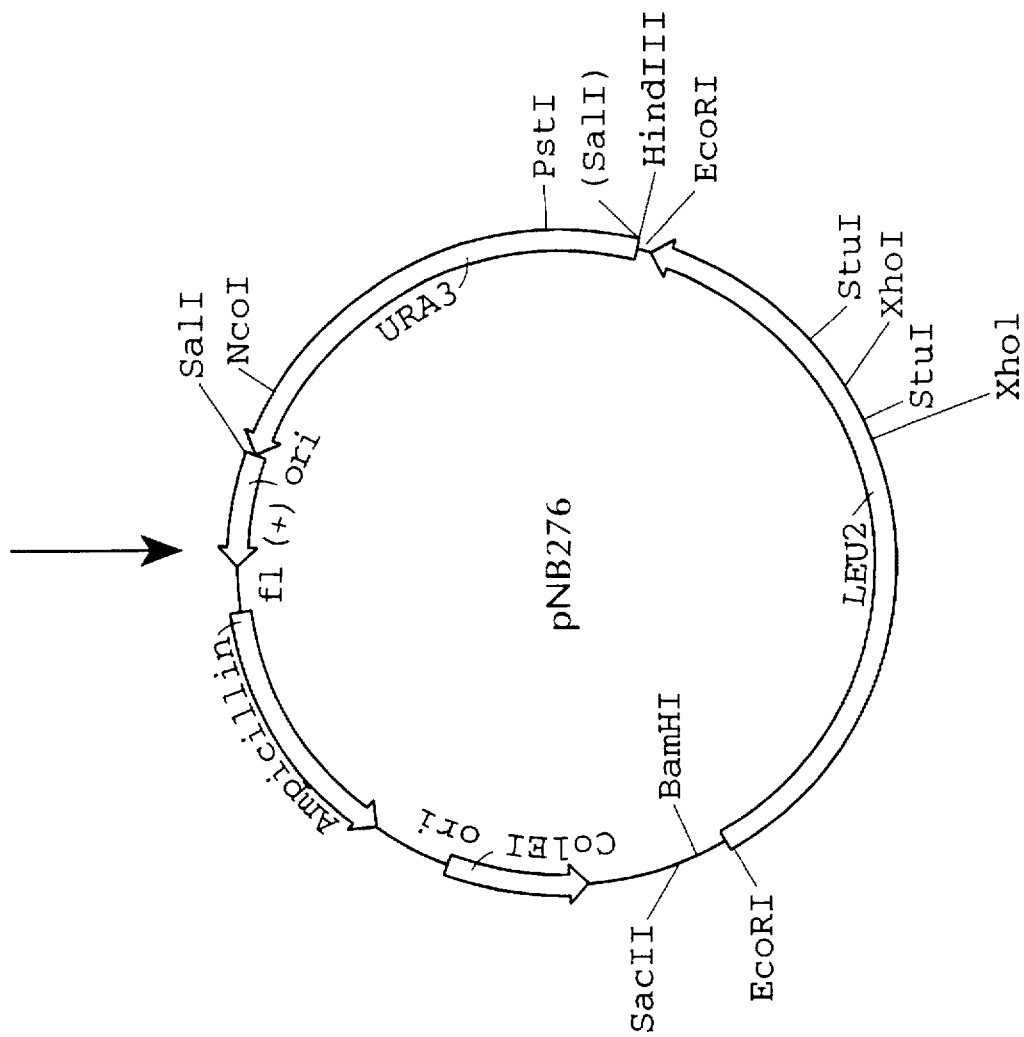

The construction of promoter-deleted LEU2 genes is presented schematically in FIG. 1. Plasmid pNB258, which serves as a template for polymerase chain reaction (PCR), includes a wild type *Y. lipolytica* URA3 gene as a positive control for transformation efficiency and to provide the ability to test the promoter-deleted LEU2 genes for the ability to complement a leucine deficient host as a single copy. To construct pNB258, a 1.6 kb blunt-ended DNA fragment containing URA3 sequences was isolated from pLD106 by digesting plasmid DNA with StuI and SalI restriction enzymes, and treating the restriction digest with Klenow fragment according to supplier's instructions. Approximately 200 ng of this DNA was ligated with approximately 500 ng of SalI digested, Klenow blunted, alkaline phosphatase-treated pBluescript+SK vector (Stratagene Cloning Systems, La Jolla, Calif.) using T4 DNA ligase according to supplier's directions. One-third of the ligation mix was transformed into *E. coli* strain DH5-α, and plated on LB plates containing 100 µg/ml ampicillin. DNA was prepared from selected single colony isolates of transformants and digested with KpnI and BamHI restriction enzymes. Restriction fragments were separated on 1% agarose gels and visualized by ethidium bromide staining. Plasmid pNB257 was identified based on the presence therein of a 1.6 kb DNA fragment containing the URA3 gene.

A LEU2 gene was constructed in which an internal EcoRI site was removed by a single base change which did not alter the LEU2 coding sequences. This LEU2 gene construct allowed the isolation of the LEU2 gene as a single EcoRI DNA fragment, which made further manipulations more convenient. This construct was generated as follows. DNA from plasmid pLD40 (which contains the LEU2 gene in pBR322 and is described in U.S. Pat. No. 4,880,741 and U.S. Pat. No. 5,071,764) was digested with XhoI, which removed a 29 base pair fragment of DNA containing an internal EcoRI site, and treated with alkaline phosphatase. Linear DNA was separated electrophoretically on a 0.7% agarose gel and electroeluted. Two hundred (200) ng of this linear DNA was ligated to 50 ng of synthetic linker DNA which contained a single base pair change (C/G to T/A at base 22) which removed the EcoRI site without changing the corresponding LEU2 codon. The synthetic linker used was of the sequence 5'-TCGAGTCCTCAAGGACGAATTTCCCCAGC-3'
(SEQUENCE ID. NO: 2)
3'-CAGGAGTTCCTGCTTAAAGGGGTCGAGCT-5'
(SEQUENCE ID. NO: 3)

wherein the changed base is underlined and which, for purposes of the Sequence Listing hereinbelow, consists of the following sequences expressed in the 5' to 3' direction:

5'-TCGAGTCCTCAAGGACGAATTTCCCCAGC-3'
(SEQUENCE I.D. NO: 2)
and
5'-TCGAGCTGGGGAAATTCGTCCTTGAGGAC-3'
(SEQUENCE I.D. NO: 3)

One fifth of the ligation mix was transformed into *E. coli* strain DH5-α and the transformants were plated on LB plates containing 100 µg/ml ampicillin. DNA was prepared from 16 transformant colonies and 1–2 µg plasmid DNA was digested with EcoRI. DNA fragments were separated electrophoretically on 0.7% agarose and visualized with ethidium bromide. Five micrograms of DNA from several plasmids, which released a single 2.5 kb EcoRI DNA fragment rather than 1.6 and 0.9 kb DNA fragments, were then digested with SacI to release a 243 bp DNA fragment containing the altered internal XhoI fragment. Fragments were separated electrophoretically on a 5% polyacrylamide gel and visualized by ethidium bromide staining. The 243 bp SacI DNA fragment from one plasmid was electroeluted and ligated with 200 ng of pBluescript+SK DNA which had been digested with SacI and treated with alkaline phosphatase. The ligation mixture was transformed into *E. coli* XL1-Blue cells (Stratagene Cloning Systems, La Jolla, Calif.) and the transformants were plated on LB plates containing 100 µg/ml ampicillin and IPTG and X-GAL as recommended by the supplier for blue-white selection. Plasmid DNA was prepared from 10 white transformant colonies, digested with SacI and fragments were separated electrophoretically on a 5% polyacrylamide gel to confirm the presence of the insert. DNA from two plasmids containing the insert was sequenced using the dideoxy chain termination method (Sequenase kit, United States Biochemical Corp. Cleveland, Ohio) to confirm the correct orientation of the XhoI DNA fragment within the LEU2 coding sequence. One of the plasmids containing a LEU2 gene with an altered internal XhoI fragment was named pLD1049.

Approximately 500 ng of DNA from pNB257 was then digested with EcoRI to linearize the plasmid, treated with alkaline phosphatase, and ligated to approximately 200 ng of a 2.5 kb EcoRI DNA fragment containing the *Y. lipolytica* LEU2 gene isolated from pLD1049. One fifth of the resulting ligation mix was transformed into *E coli* strain DH5-α, and the transformants were plated on LB plates containing 100 µg/ml ampicillin. Plasmid DNA was prepared from a number of transformant colonies and 1–2 µg of each plasmid DNA was digested with EcoRI. DNA fragments were separated electrophoretically on 0.7% agarose and visualized with ethidium bromide. A transformant containing the 2.5 kb EcoRI DNA fragment containing the LEU2 gene was designated as pNB258. Plasmid pNB258 has been deposited in the form of an *E. coli* DH5α-transformant in the American Type Culture Collection as described hereinbelow and has been assigned deposit number ATCC 69353.

A series of deletions in the *Y. lipolytica* LEU2 gene promoter nucleotide sequence were prepared as follows. The below described deletions generated from SEQUENCE I.D. NOS: 4 through 8 and 12 were spaced at about 50 base pair intervals. Deletions generated from SEQUENCE I.D. NOS: 9, 10 and 11 made single base changes within the presumed "TATA" box of the LEU2 gene such that, for SEQUENCE I.D. NO. 9 the nucleotide at position 724 of the LEU2 gene was changed from A to G; for SEQUENCE I.D. NO. 10, the nucleotide at position 725 of the LEU2 gene was changed from T to G; and for SEQUENCE I.D. NO. 11, the nucleotide at position 722 of the LEU2 gene was changed from A to G. Further, the primers were designed to provide appropriate restriction enzyme sites, e.g. BamHI and EcoRI, for subsequent use in subcloning of the sequences to be generated. It will be appreciated by those skilled in the art enabled by this disclosure that any deletion or series of deletions at any interval or intervals can be prepared according to this invention as well as by the use of other appropriate restriction sites.

The following 5' primers were synthesized using the Milligen Cyclone Plus Synthesizer (Model 8400; Millipore Corp., Bedford, Mass.). As discussed above, the primers were designed to result in nucleotide sequences having various 5' termini but also containing restriction enzyme sites suitable for subsequent subcloning. Tabulated below are the primers that were prepared.

TABLE I

| Nucleotide Sequence | Sequence I.D. NO: | 5' Terminus of Resulting LEU 2 Gene |
|---|---|---|
| GCAGGATCCG AATTCCTTGA CGATCTCGTA TGTC | 4 | 559 |
| GCAGGATCCG AATTCGCTGG GGTACGTTCG ATAG | 5 | 599 |
| GCAGGATCCG AATTCTAGCC GATACCGCAC TACC | 6 | 648 |
| GCAGGATCCG AATTCTCTTC CACATAGCAC GGGC | 7 | 693 |
| GCAGGATCCG AATTCCGTAT ATATACAAGA GCGTTTGCC | 8 | 718 |
| GCAGGATCCG AATTCCGTAT GTATACAAGA GCGTTTGCC | 9 | 718 |
| GCAGGATCCG AATTCCGTAT AGATACAAGA GCGTTTGCC | 10 | 718 |
| GCAGGATCCG AATTCCGTGT ATATACAAGA GCGTTTGCC | 11 | 718 |
| GCAGGATCCG AATTCCCACA GATTTTCACT CC | 12 | 745 |

Each of the primers listed in Table I, above, contains a restriction enzyme recognition site for BamHI and EcoRI towards the 5' end thereof.

The *Y. lipolytica* LEU2 structural gene nucleotide sequence begins at nucleotide 799 of SEQUENCE I.D. NO: 1. A 3' primer was prepared and the sequence thereof was chosen to include a convenient restriction site within the structural coding region of the LEU2 gene. The site chosen was a StuI site which is located at nucleotide 919 of SEQUENCE I.D. NO: 1. Of course, other appropriate restriction enzyme sites could be used. The 3' primer used in the constructions discussed below contained the nucleotide sequence CACAAACTCG GTGCCGGAGG CC (SEQUENCE I.D. NO: 13). The 3' primer was prepared according to the method described above for the preparation of the 5' primers listed in Table I.

The method of polymerase chain reaction (PCR) was used to prepare multiple copies of nucleotide sequences having 5' termini corresponding to the 5' termini of the primers listed in Table I, above, and having 3' termini corresponding to the 3' terminus of the 3' primer of SEQUENCE I.D. NO: 13. The PCR was conducted using a Perkin-Elmer-Cetus PCR Reagent Kit (Catalog N801-0055) in a Perkin-Elmer Cetus DNA Thermal Cycler (Norwalk, Conn.). The reaction mixture contained 10 mM Tris-HCl, pH8.3, 50 mM KCl, 1.5 mM $MgCl_2$, 200 µM each of dATP, dCTP, dGTP and dTTP, 1 µM of the 5' primer, 1 µM of the 3' primer, 2.5 units of ampliTaq DNA polymerase and approximately 10 ng of pNB258 DNA in a total volume of 100 µL. The reaction was run for 30 cycles using the following parameters: melt at 94° C. for 1.5 min., anneal at 50° C. for 2 min., extend at 72° C. for 3 min.

Modified *Y. lipolytica* LEU2 genes with deleted promoters were constructed as follows and as depicted in FIG. 1. Each PCR generated DNA fragment, prepared as described immediately above, was digested with BamHI and StuI, and gel isolated. Plasmid pNB258 DNA was digested with BamHI and StuI to remove the wild-type LEU2 promoter and LEU2 coding sequences up to the StuI site which formed the 3' end of each PCR-generated DNA fragment as well as a 0.68 kb StuI DNA fragment internal to the LEU2 gene. The 6.2 kb BamHI-StuI DNA vector fragment as well as the 0.68 kb StuI internal DNA fragment were gel-isolated using electrophoresis. Approximately 200 ng of each PCR-generated fragment was then ligated in separate reactions to approximately 500 ng of the 6.2 kb BamHI-StuI DNA fragment and 200 ng of the 0.68 kb StuI DNA fragment. Approximately one-fifth of each ligation mix was transformed into *E. coli* DH5-α, and the transformants were plated on LB plates containing 100 µg/ml ampicillin. Plasmid DNA was prepared from a number of transformants and digested separately with EcoRI and StuI restriction enzymes to identify those plasmids which contained the correct DNA fragments. Correct plasmids were sequenced by the dideoxy chain termination method (TaqTrack Sequencing System, Promega, Madison Wis.) using as primer one or more of the following oligodeoxynucleotides (synthesized as described previously (SEQUENCE I.D. NOS: 5 and 14) or commercially available (T3 primer; Stratagene Cloning Systems, La Jolla Calif.)):

(1) 5'-CTCCTCCAATGAGTCGG-3' (SEQUENCE I.D. NO: 14); this primer hybridized to LEU2 gene sequences within the internal 0.68 kb StuI DNA fragment and was designed to generate DNA sequence information upstream from the StuI site at the 3' end of the PCR DNA fragment;

(2) SEQUENCE I.D. NO: 5; this primer hybridized to LEU2 sequences 5' of the open reading frame and generated sequence information from the 3' end of the promoter region downstream through the LEU2 open reading frame; and (3) A commercially available T3 primer which hybridized to vector sequences upstream of the 5' end of the PCR-generated DNA fragment.

DNA sequence information thus generated was used to determine that the internal StuI DNA fragment was oriented correctly and that each PCR-generated DNA sequence was authentic.

2. CONSTRUCTION OF *Y. lipolytica* HOST STRAIN WITH DELETED LEU2 GENE (LEU2Δ).

Figure 2A:
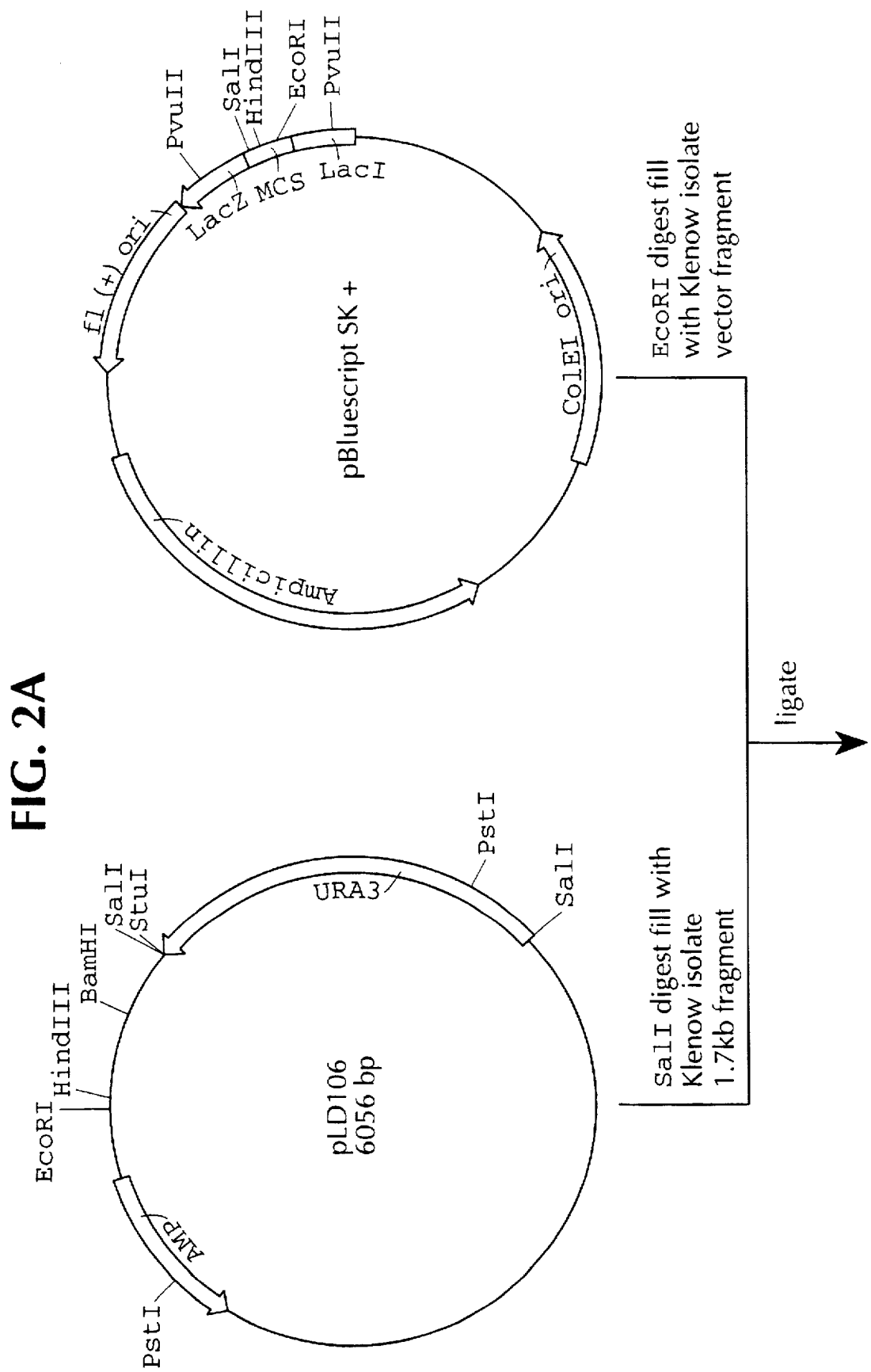
FIGS. 2A–2C are schematic representations of the construction of plasmid pNB243.
Figure 2B:
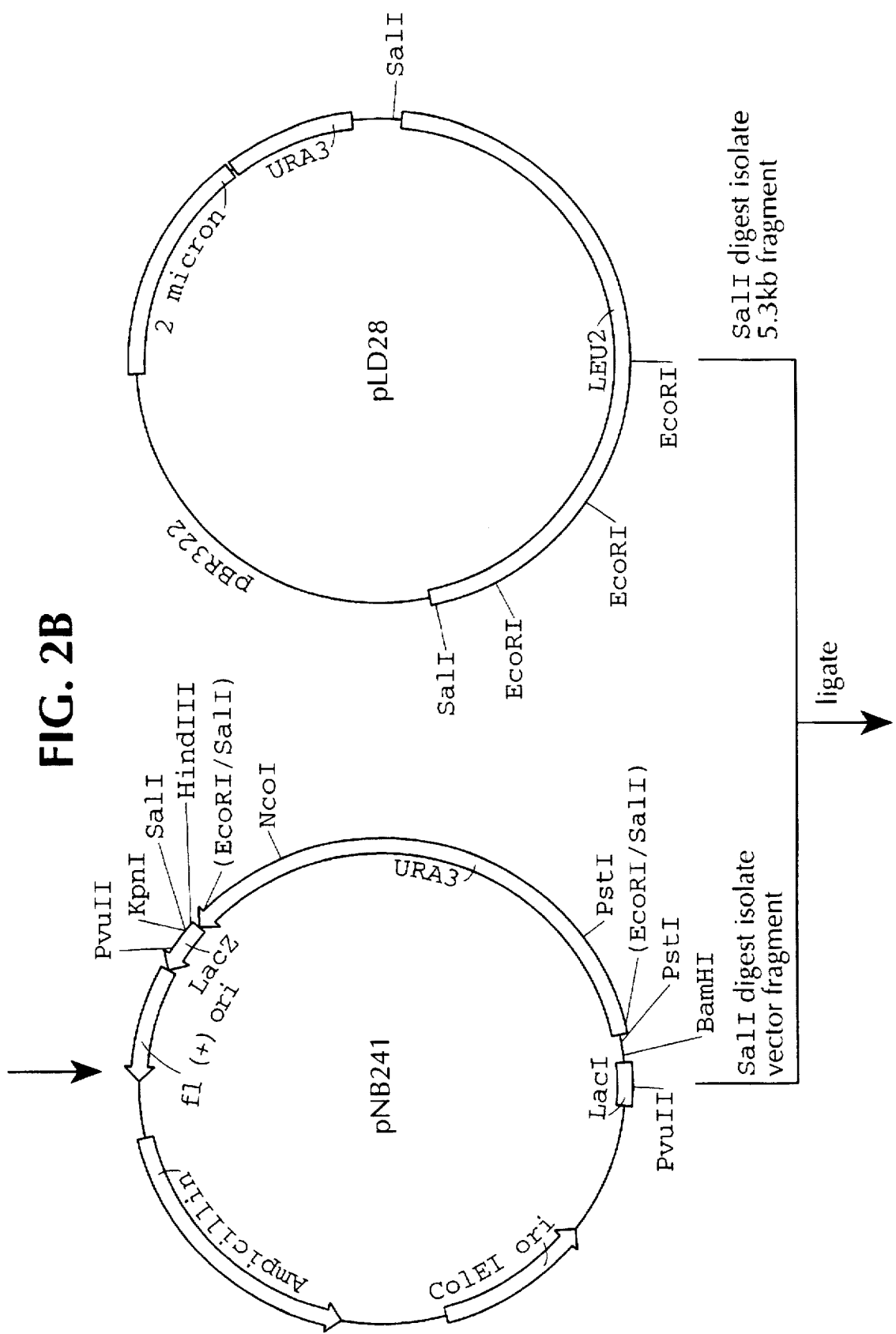
Figure 2C:
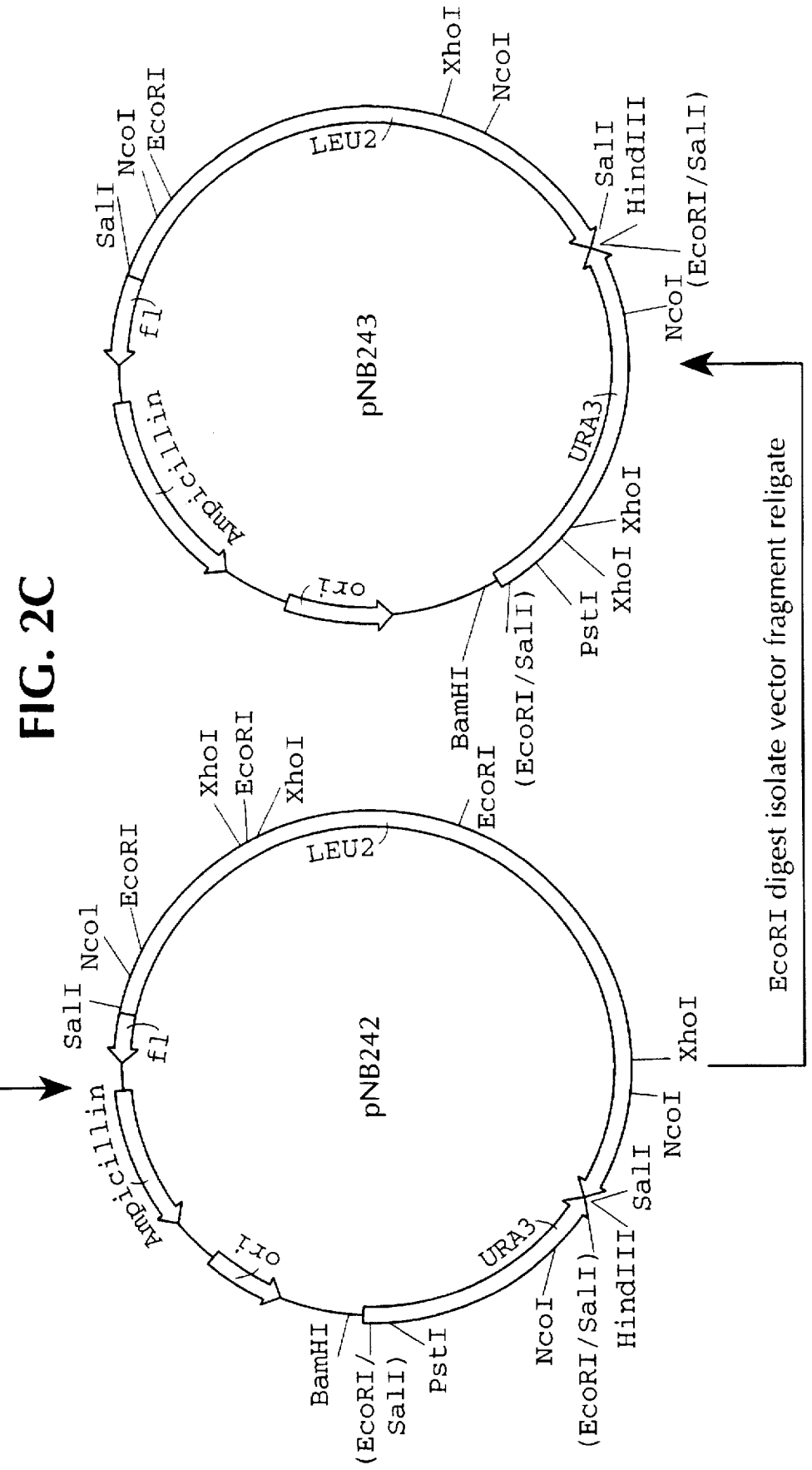

*Y. lipolytica* host strains wherein the LEU2 sequences homologous to the sequences of the defective LEU2 genes of this invention are deleted were constructed. To construct such strains, the following plasmid (pNB243) was prepared. The construction of that plasmid is schematically depicted in FIG. 2. The 1.7 kb SalI fragment containing the URA3 gene from pLD106 was converted to blunt ends by filling in with the large fragment of Klenow polymerase and approximately 200 ng of the 1.7 kb SalI blunted fragment was ligated to approximately 500 ng of EcoRI-digested, Klenow blunted Bluescript $SK^+$ vector (Stratagene Cloning Systems, La Jolla, Calif.). A blunted URA3 gene can also be recovered from pNB258, described hereinabove, by, for example, digestion with KpnI and HindIII and blunting with T4 DNA polymerase. Approximately one-fifth of the ligation mix was transformed into *E. coli* strain DH5-α and the transformants were plated onto LB plates containing 100 µg/ml ampicillin. Plasmid DNA was prepared from a number of transformants and digested with HindIII and BamHI restriction enzymes. Fragments were separated electrophoretically on a 1.0% agarose gel and visualized by staining with ethidium bromide.

The correct plasmid contained a 1.7 kb DNA fragment containing URA3 sequences and was named pNB241. Five hundred nanograms of pNB241 DNA was then digested with SalI, treated with alkaline phosphatase and ligated together with 200 ng of a 5.3 kb SalI DNA fragment from pLD28 which contained LEU2 coding sequences along with DNA sequences flanking LEU2 in the *Y. lipolytica* chromosome. Plasmid pLD28 is described in U.S. Pat. No. 5,071,764 and is described and claimed in U.S. Pat. No. 4,880,741. Approximately one-fifth of the ligation mix was transformed into *E. coli* strain DH5-α and the transformants were plated onto LB plates containing 100 µg/ml ampicillin. DNA was prepared from a number of transformants and digested with SalI. Fragments were separated electrophoretically on a 1.0% agarose gel and visualized by staining with ethidium bromide. Digestion of the correct plasmid released a 5.3 kb SalI DNA fragment. This plasmid was named pNB242. DNA from plasmid pNB242 was then digested with EcoRI to release 1.6 and 0.9 kb DNA fragments containing LEU2 coding sequences. The remaining 7.4 kb linear vector was electrophoretically gel isolated, ligated and the ligation mix used to transform *E. coli* strain DH5-α. Transformants were plated on LB plates containing 100 µg/ml ampicillin. DNA was isolated from a number of transformants, digested with SalI and fragments were separated electrophoretically on a 1.0% agarose gel. The correct plasmid (pNB243) contained a 2.8 kb SalI DNA fragment.

Plasmid pNB243 contains three XhoI restriction sites: two within the URA3 gene and one within the 2.8 kb SalI DNA fragment of LEU2. Plasmid pNB243 was partially digested with XhoI to linearize the vector as follows. Approximately 2 µg of pNB243 DNA was treated respectively with 10 units of XhoI enzyme for 5, 10 and 20 minutes at 37° C. The reaction was stopped by ethanol precipitation of the reaction mixture and samples of the digested DNA were analyzed electrophoretically on a 0.8% agarose gel. The five minute time point, which gave the highest proportion of 7.4 kb linear vector, was chosen to use for transformation of *Y. lipolytica* strain NBL369 (MATB,bio6::BIO(pBR322), leu2-40, xpr2-1002, ura3Δ). Transformants were plated on minimal medium lacking uracil to select for Ura+ transformants. DNA was isolated from a number of Ura+ transformants and digested separately by SphI and SalI. The resulting DNA fragments were separated by agarose gel electrophoresis and transferred to Hybond N nylon membrane (Amersham Corp., Arlington Heights, Ill.). The membranes were hybridized to a 2.4 kb EcoRI-SalI DNA fragment of LEU2 from pNB243. The disappearance of the parental 7.5 kb SphI LEU2 DNA fragment and the appearance of a new approximately 16 kb SphI DNA fragment indicated that the vector had integrated properly at the LEU2 locus. The appearance of both the 5.3 kb SalI (parental) and 2.9 kb SalI (deletion) LEU2 DNA fragments verified that both the wild-type and the deletion LEU2 genes were present. Two such transformants were named NBL461 and NBL462.

NBL461 and NBL462 were grown under non-selective conditions on rich YPD medium for two days to allow for loss or "pop-out" of the URA3 marker by homologous recombination. The cells were then plated onto 5-fluorouracil selection plates supplemented with leucine and uracil as described by Boeke, J. D., et al., Methods in Enzymology 154: 164–175 (1987). DNA was prepared from several 5-fluorouracil (ura⁻) survivors, digested with SalI and screened by Southern hybridization analysis as described above using the 0.4 kb SalI-EcoRI fragment of pNB243 as a probe. Two of the transformants, NBL463 and NBL464, had lost the wild-type sized SalI fragment, and had retained only the leu2Δ-sized SalI fragment.

The strains listed below were deposited on Jul. 22, 1993, under the terms of the Budapest Treaty in the American Type Culture Collection, 12301 Parklawn Drive, Rockville, Md. 20852, United States of America, a recognized depository affording permanence of the deposits and ready accessibility thereto by the public if a patent is granted on this application. The deposits are available during the pendency of this application to one determined by the Commissioner of the United States Patent and Trademark Office to be entitled thereto under 37 CFR 1.14 and 35 U.S.C. 122, and in accordance with foreign patent laws in countries wherein counterparts of this application, or its progeny, are filed. All restrictions on the availability to the public of the microorganisms deposited will be irrevocably removed upon granting of the patent.

| STRAIN | ATCC Deposit Number |
| --- | --- |
| *Y. lipolytica* NBL464 | ATCC 74234 |
| *E. coli* DH5-α/pNB258 | ATCC 69353 |
| *E. coli* DH5-α/pNB650 | ATCC 69354 |
| *E. coli* DH5-α/pNB268 | ATCC 69355 |

3. EVALUATION OF DEFECTIVE LEU2 GENES.

To evaluate the LEU2 gene promoter deletion plasmids which were prepared as described above, *Y. lipolytica* leu 2Δ strain NBL464(ATCC 74234) was transformed separately by pNB258 and each of the LEU2 promoter deletion plasmids. Each plasmid was digested with PstI prior to transformation in order to target integration by homologous recombination to the ura3Δ region of the *Y. lipolytica* chromosome. The transformants were selected on complete minimal medium without uracil and the Ura⁺ transformants were then screened for the Leu phenotype by their ability to grow on complete minimal medium lacking leucine. Tabulated below are the results of that screen.

TABLE II

| Plasmid | Growth on Complete Minimal Medium minus Leucine |
| --- | --- |
| pNB258 | Good |
| pNB271 | Good |
| pNB272 | Good |
| pNB276 | Weak |

Plasmid pNB276 contains a weakly-complementary LEU2 gene and, hence, contains a defective LEU2 gene promoter having its 5' terminus at position 693 of the LEU2 gene. Other LEU2 promoter deletion genes produced according to this invention and contained in plasmids designated pNB656 (5' terminus at position 718 of the LEU2 gene), pNB652 (5' terminus at position 718 of the LEU2 gene and containing nucleotide G instead of A at position 724), pNB653 (5' terminus at position 718 of the LEU2 gene and containing nucleotide G instead of T at position 725), pNB654 (5' terminus at position 718 of the LEU2 gene and containing nucleotide G instead of A at position 722) and pNB313 (5' terminus at position 745 of the LEU2 gene) provided similar results.

4. CONSTRUCTION OF MULTIPLE-INTEGRATION VECTOR COMPRISING rDNA SEQUENCES.

Figure 3A:
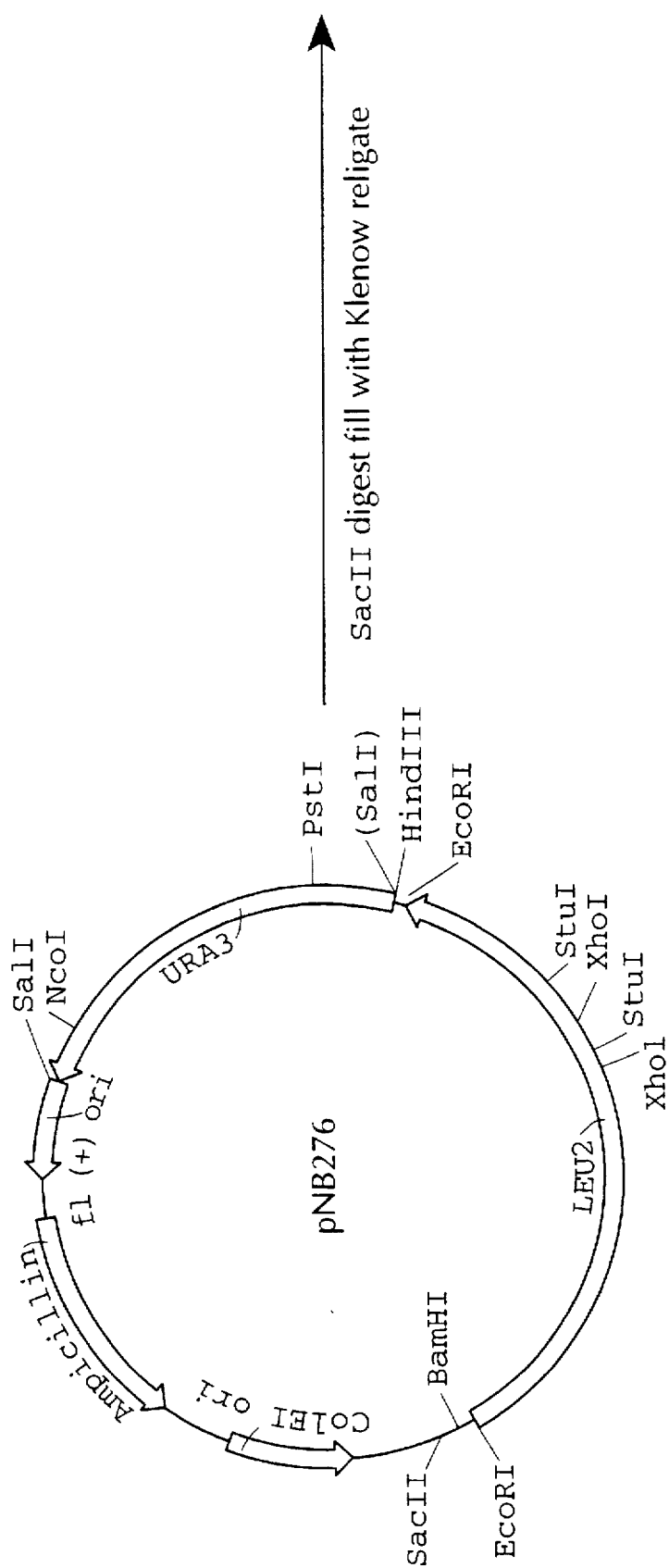
FIGS. 3A–3C are schematic representations of the construction of plasmid pNB308.
Figure 3B:
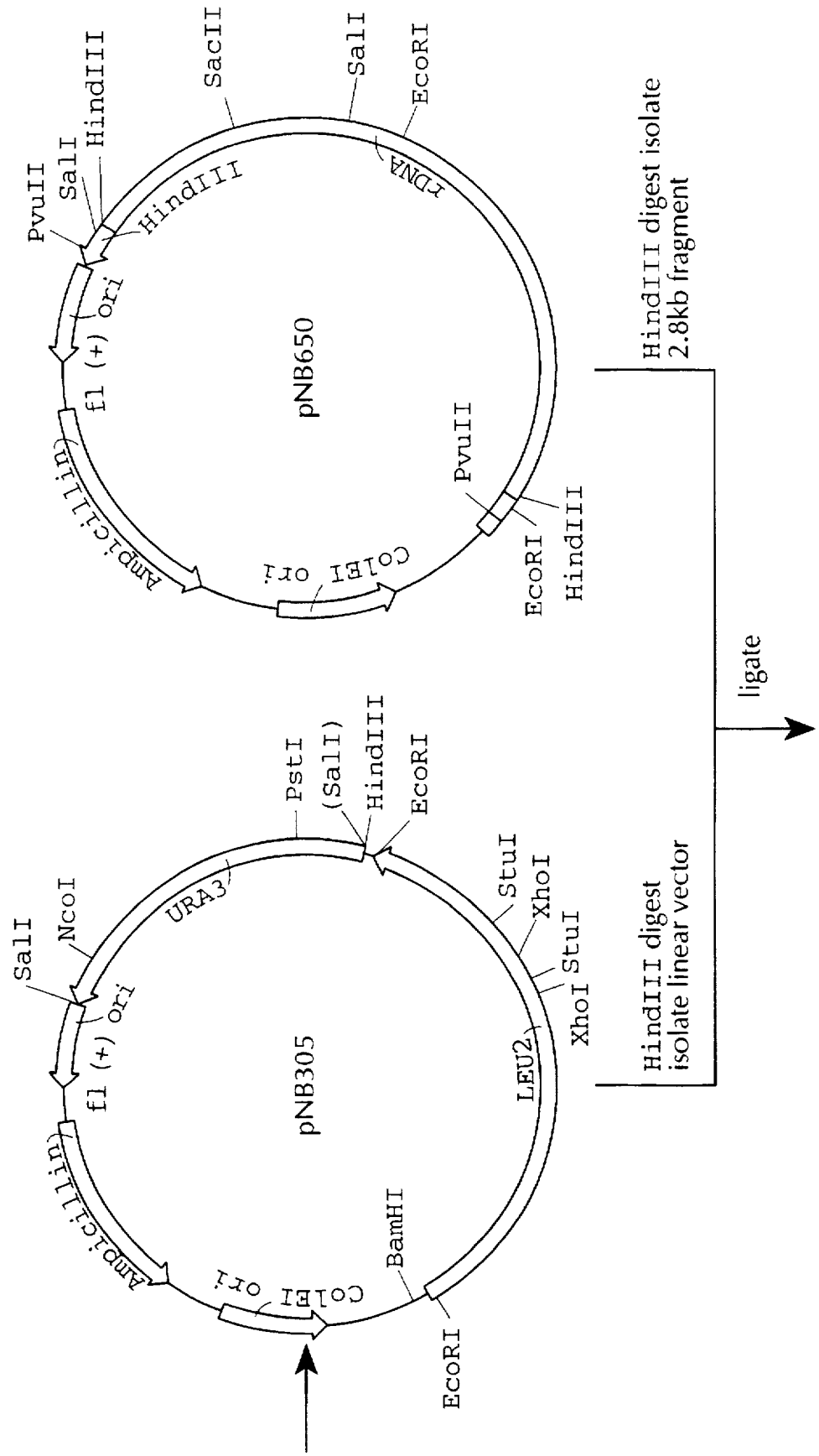
Figure 3C:
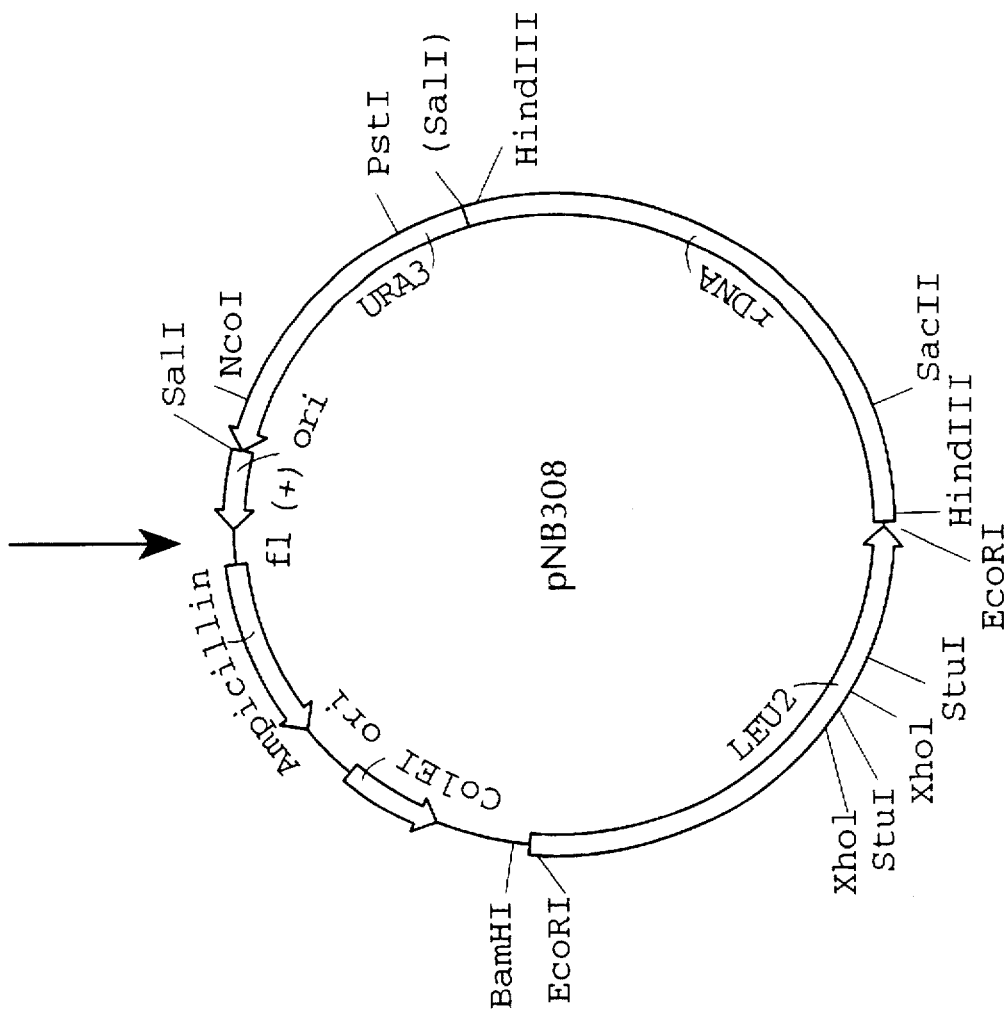
Figure 4A:
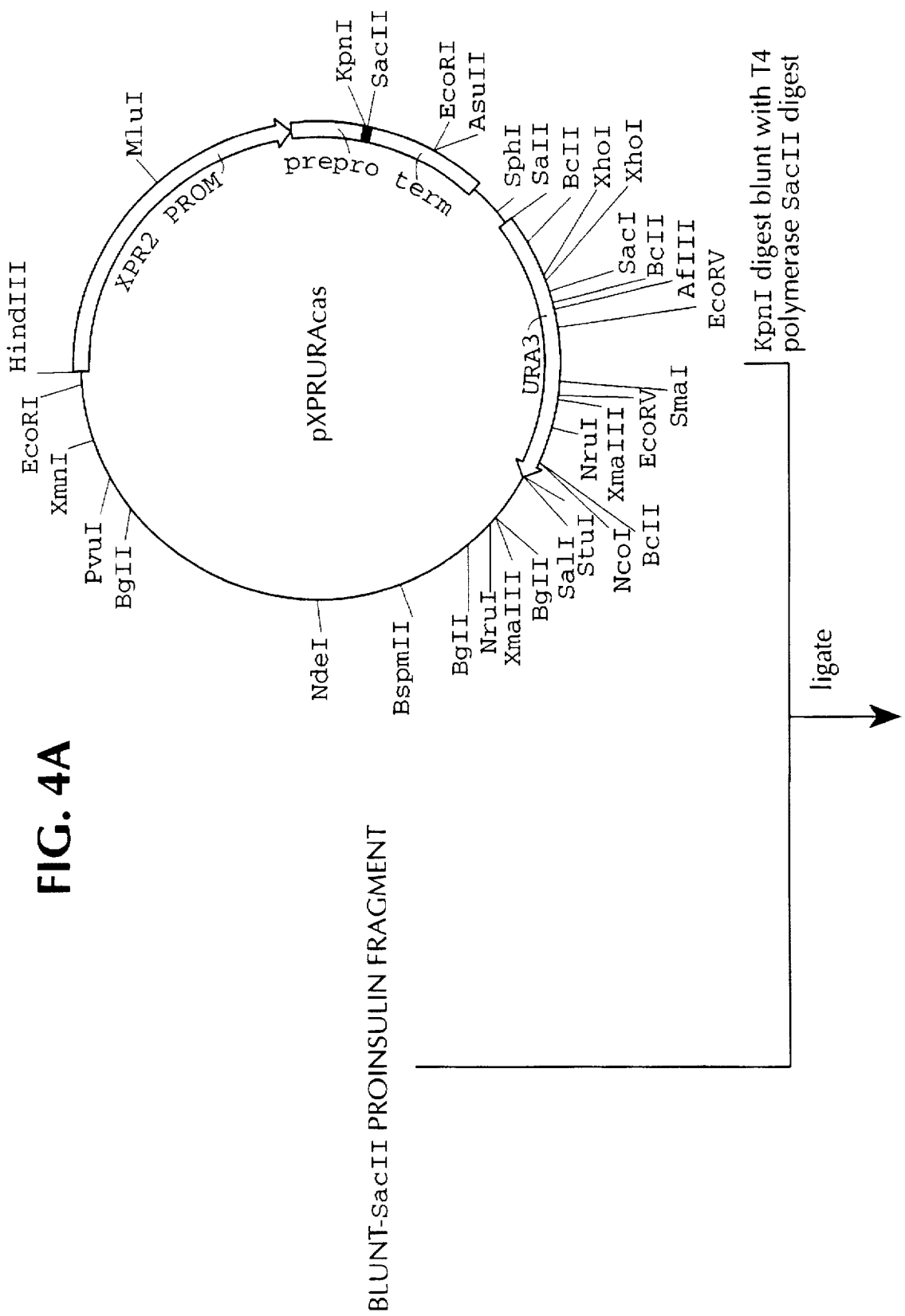
FIGS. 4A–4F are schematic representations of the construction of plasmid pMIVINS.
Figure 4B:
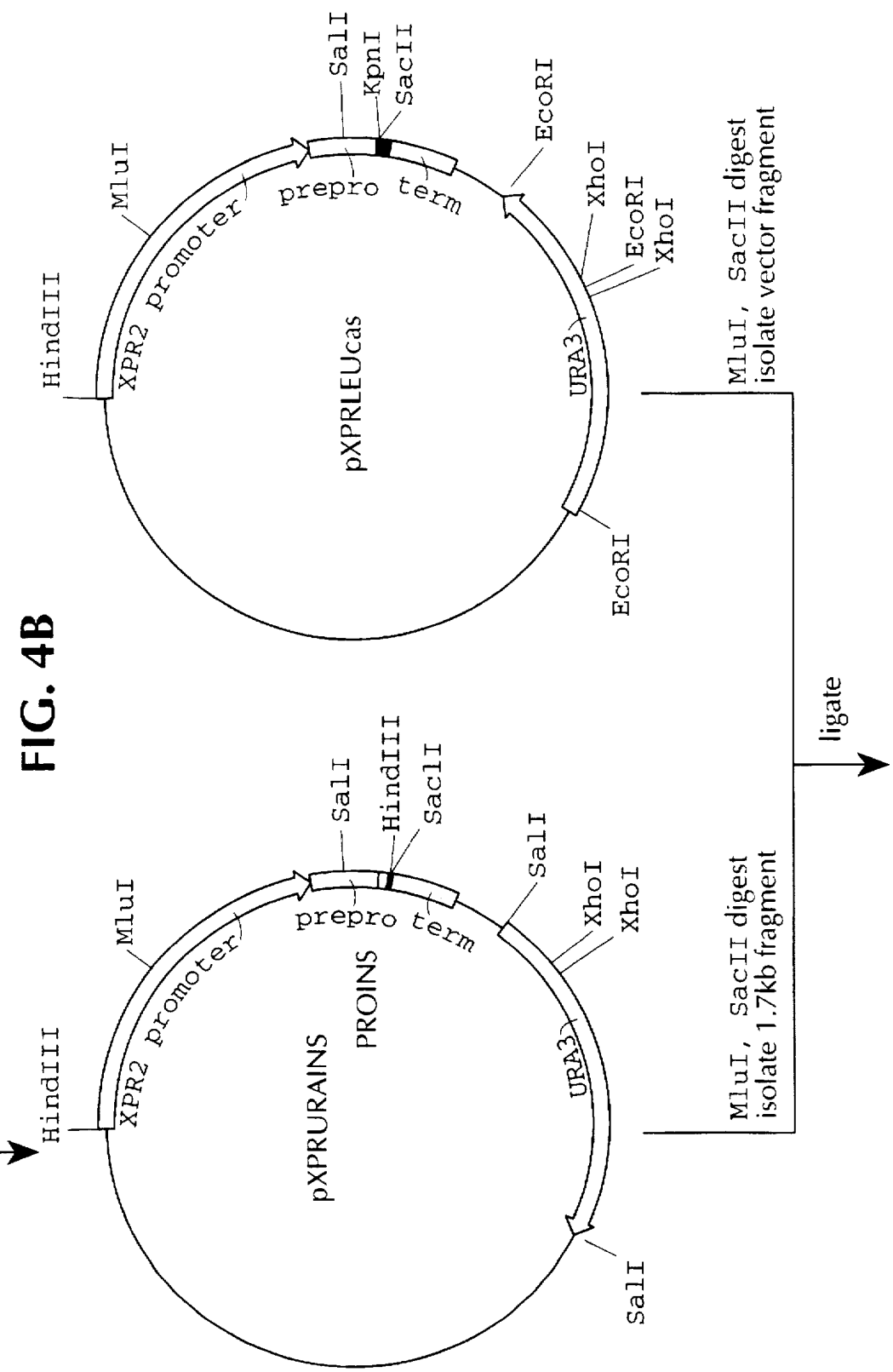
Figure 4C:
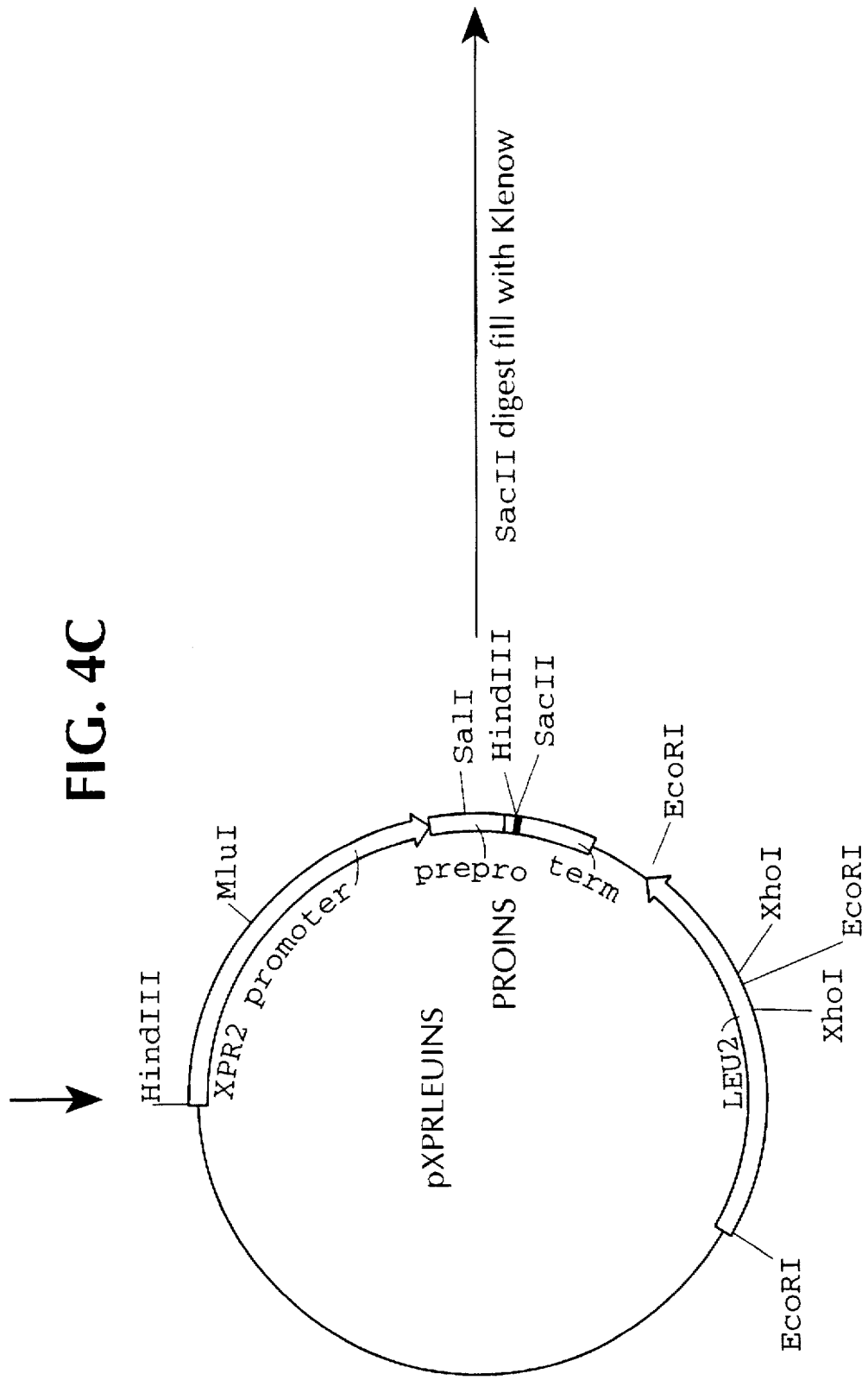
Figure 4D:
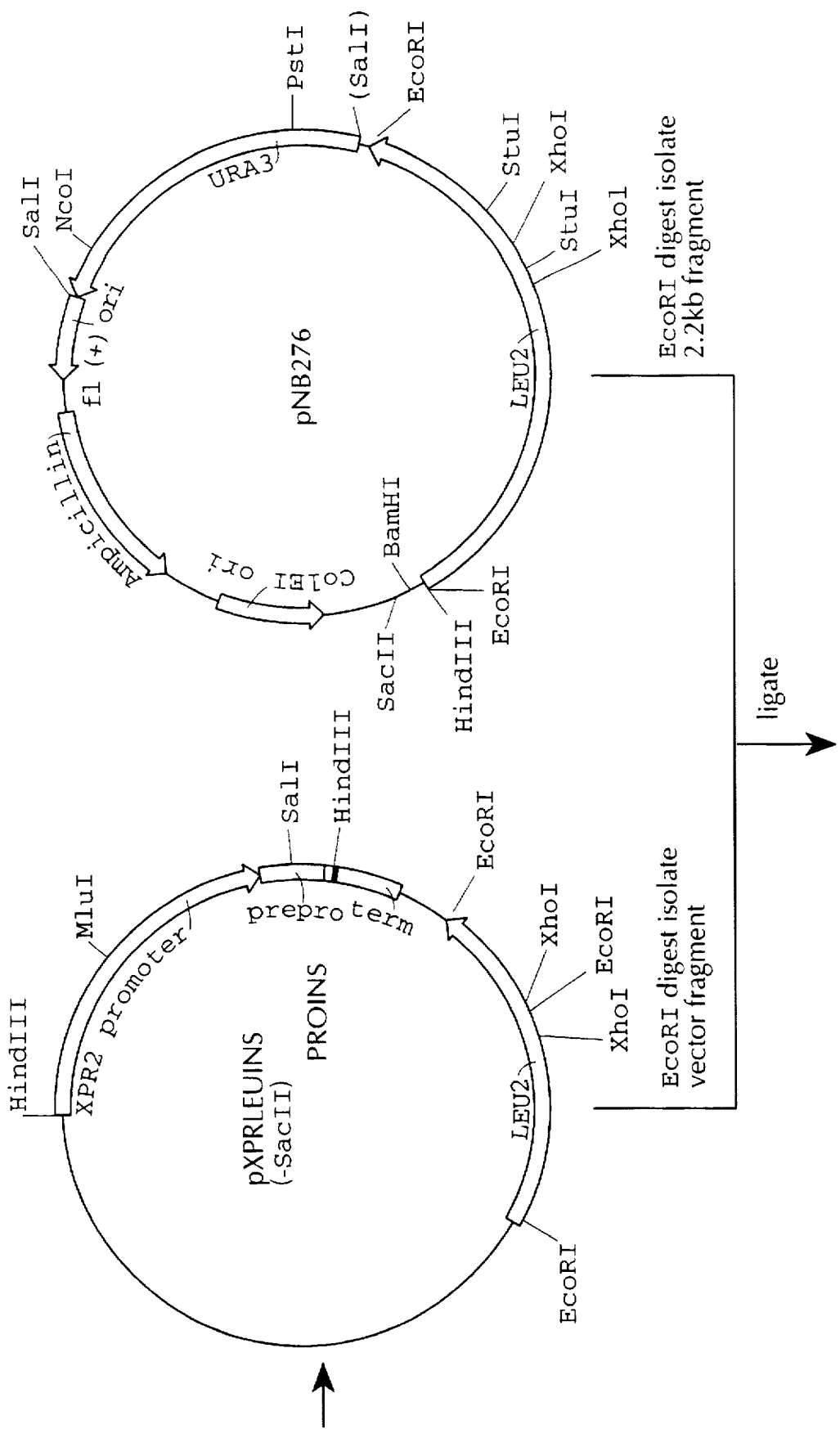
Figure 4E:
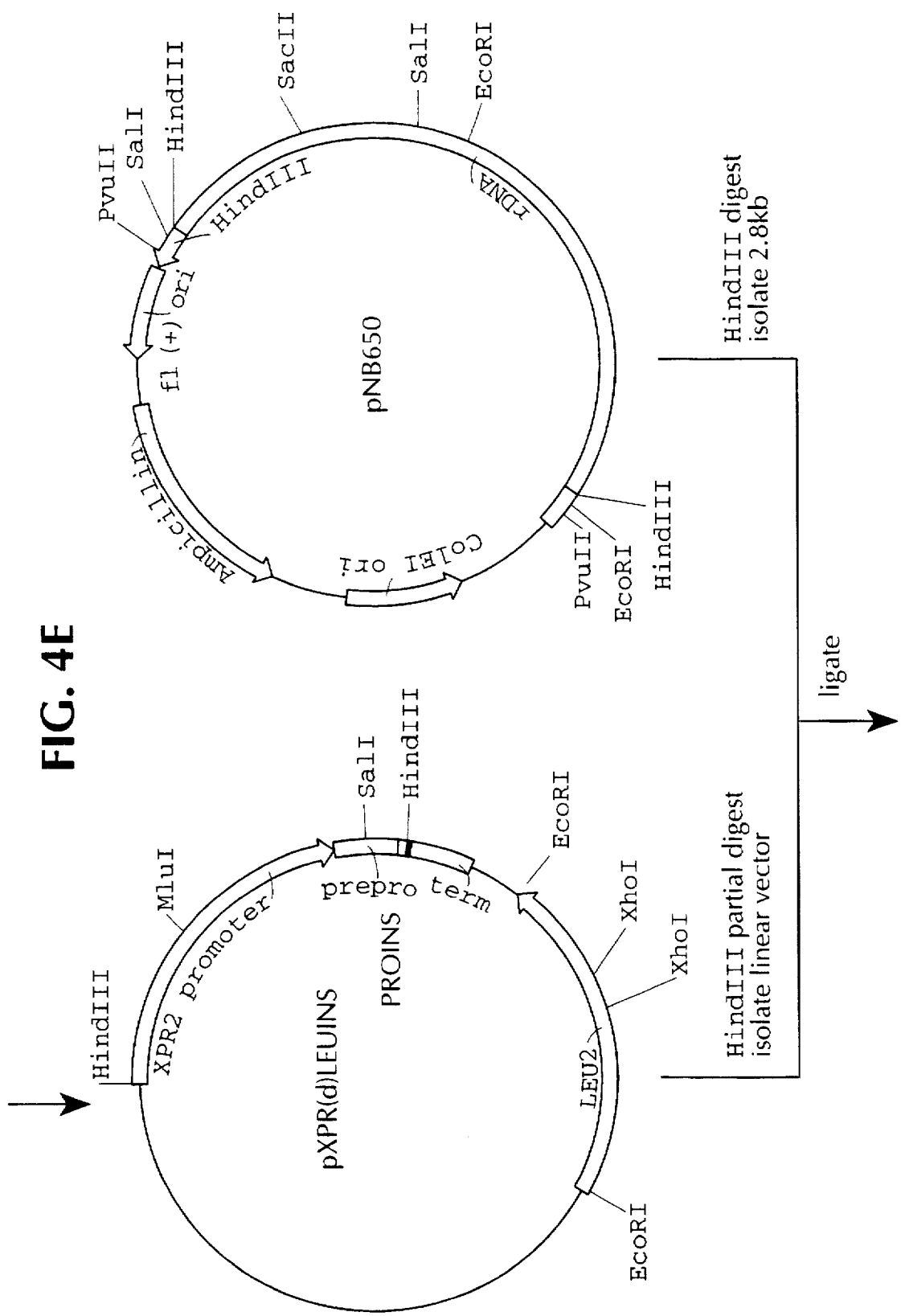
Figure 4F:
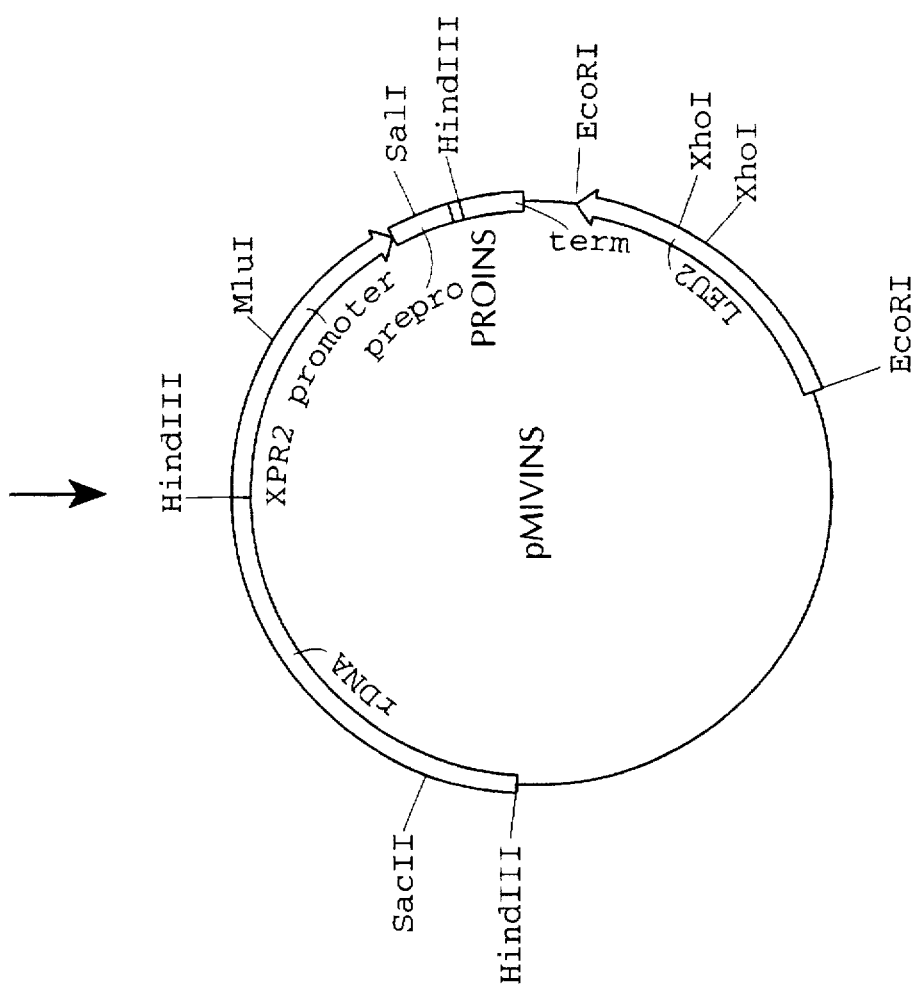

Construction of a multiple integration vector (pNB308) is schematically depicted in FIG. 3. Plasmid pNB276, prepared and identified as described above, was modified by deleting the SacII site within the polycloning region of the plasmid. The deletion was accomplished by digesting pNB276 with SacII. Then, the SacII digested pNB276 was made blunt-ended with Klenow fragment and then blunt-end ligated. The blunt-end ligated plasmids were used to transform *E. coli* DH5-α and the correct construct (pNB305) was identified by restriction analysis. Ribosomal DNA (rDNA) sequences were isolated from pNB650 by digesting plasmid DNA with HindIII. pNB650 contains a 2.8 kb NcoI fragment of rDNA (Clare, J. J., et al., Curr Genet 10:449–452 (1986)), in which the NcoI sites have been converted to HindIII sites by blunting with Klenow fragment and ligating to HindIII linkers followed by ligation to HindIII-digested pBluescript+SK (Stratagene Cloning Systems, La Jolla, Calif.). Plasmid pNB650 has been deposited with the American Type Culture Collection in the form of an *E. Coli* DH5-α transformant and has been assigned deposit number ATCC 69354 as described above. The 2.8 kb HindIII rDNA containing fragment from pNB650 was isolated by standard agarose gel electrophoresis methods. The isolated 2.8 kb HindIII rDNA fragment was then ligated to HindIII digested pNB305. The resulting ligation mixture was used to transform *E. coli* DH5-α. DNA from a number of transformants was digested by HindIII and fragments separated electrophoretically on a 0.7% agarose gel. The correct plasmid contained a 2.8 kb HindIII DNA fragment and was named pNB308.

5. CONSTRUCTION OF MULTIPLE INTEGRATION VECTOR CONTAINING STRAINS OF *Y. lipolytica*.

Plasmid pNB308, prepared as described above, was digested with SacII which cuts one time within the rDNA sequence in the plasmid. The linear plasmid was thus targeted to integrate by homologous recombination with the repeated rDNA sequences of the host *Y. lipolytica* strain. Strain *Y. lipolytica* NBL464 (ATCC 74234) was transformed with SacII digested pNB308 according to the standard procedure described above. Transformants were selected on complete minimal medium without leucine. There appeared Leu⁺ transformants of large and small colony type.

DNA was isolated from large transformant colonies, digested with SalI, run on an agarose gel, transferred to Hybond N membranes, and probed with a 0.49 kb BstXI-SalI fragment of URA3 DNA which would hybridize both to the single copy chromosomal ura3Δ gene (on a 1.0 kb SalI fragment) as well as to each copy of URA3 contributed by pNB308 (on a 3.5 kb SalI fragment). Hybridization signals were quantitated using a Beta-Scope 603 Blot Analyzer (Betagen, Waltham, Mass.), and plasmid copy number for each transformant was determined by calculating the fold difference in total counts for the 3.5 kb band compared with the 1.0 kb band. Summarized in Table III, below, are the copy numbers for the transformants studied by Southern analysis.

TABLE III

| Transformant | MIV Copy Number |
| --- | --- |
| 1 | 3 |
| 2 | 3 |
| 3 | 2 |

TABLE III-continued

| Transformant | MIV Copy Number |
| --- | --- |
| 4 | 2 |
| 5 | 4 |
| 6 | 5 |
| 7 | 6 |
| 8 | 12 |
| 9 | 11 |
| 10 | 8 |
| 11 | 5 |
| 12 | 5 |
| 13 | 6 |
| 14 | 4 |
| 15 | 4 |
| 16 | 3 |
| 17 | 5 |
| 18 | 11 |
| 19 | 6 |
| 20 | 4 |

To confirm that the vector was integrated within rDNA sequences, transformant DNA was digested with SacII, which cuts once within the plasmid within rDNA sequences, run on an agarose gel, transferred to Hybond N membranes, and probed with a 0.49 kb BstXI-SalI DNA fragment from URA3. A 10.8 kb band, the size of the intact plasmid, was detected, which confirmed that the vector had integrated within rDNA sequences and without major rearrangement.

The stability of transformants 8 and 9 was studied. Transformants 8 and 9 were inoculated 1:100 into separate YPD medium, grown 24 hours at 28° C., diluted 1:100 into fresh YPD medium and regrown for a total of three cycles. Cells were sampled at 24, 48 and 72 hours (corresponding to approximately 12, 24 and 36 generations). DNA was prepared from the cell samples and analyzed for copy number as described above. The copy numbers of transformants 8 and 9 did not change during continued growth in rich, non-selective medium.

7. CONSTRUCTION OF PROINSULIN ANALOG MULTIPLE INTEGRATIVE EXPRESSION VECTOR.

The starting plasmid in the construction of a proinsulin analog multiple integrative expression vector was plasmid pXPRURAcas, which contains the XPR2 promoter, pre- and pro-sequences followed by a multiple cloning site, and XPR2 terminator sequences along with a wild-type URA3 gene as selectable marker. The construction of a proinsulin analog multiple integrative expression vector is shown in FIG. 4. Plasmid pXPRURAcas was digested with KpnI, blunted by treatment with T4 polymerase, and redigested with SacII. This vector fragment was ligated to a proinsulin analog (A14trp) coding sequence provided by Scios Nova, Inc., Mountainview, Calif. which had the following sequence along with 5'-blunt and 3'-SacII restriction ends:

```
TTTGTGAACC AACACCTGTG CGGATCCCAC CTGGTGGAAG CTCTCCACCT

AAACACTTGG TTGTGGACAC GCCTAGGGTG GACCACCTTC GAGAGGTGGA

AGTGTGCGGG GAACGAGGCT TCTTCTACAC ACCCAAGACC CGCCGGAGGG

TCACACGCCC CTTGCTCCGA AGAAGATGTG TGGGTTCTGG GCGGCCTCCC

CAGAGGACCT GCAGGTGGGG CAGGTGGAGC TGGGCGGGGG CCCTGGTGCA

GTCTCCTGGA CGTCCACCCC GTCCACCTCG ACCCGCCCCC GGGACCACGT

GGCAGCCTGC AGCCCTTGGC CCTGGAGGGG TCCCTGCAGA AGCGTGGCAT

CCGTCGGACG TCGGGAACCG GGACCTCCCC AGGGACGTCT TCGCACCGTA

TGTGGAACAA TGCTGTACCA GCATCTGCTC CCTCTACCAG CTGGAGAACT

ACACCTTGTT ACGACATGGT CGTAGACGAG GGAGATGGTC GACCTCTTGA

ACTGCAACTA GAAGCTTGGC CGC

TGACGTTGAT CTTCGAACCG G
```

For purposes of the Sequence Listing hereinbelow, that sequence is represented as SEQUENCE I.D. NO: 14 for the 5'-3' single strand and SEQUENCE I.D. NO: 15 for the 3'-5' single strand, though presented as the corresponding 5'-3' strand in SEQUENCE I.D. NO: 15.

This ligation created an in-frame fusion between the last codon of the *Y. lipolytica* XPR2 pro region and the first codon of proinsulin analog A14trp. Part of the ligation mix was transformed into *E. coli* DH5-α, and the transformants were plated on LB containing 100 µg/ml ampicillin. Plasmid DNA was prepared from a number of transformants, digested with Hind III, and the fragments separated electrophoretically on 0.8% agarose gels. The correct construction showed release of a 2.8 kb HindIII DNA fragment due to introduction of an additional HindIII site within the proinsulin analog gene fragment. Several positive clones were identified and sequenced to ensure the fidelity of the junction sequence between the XPR2 pro region and the proinsulin gene, as well as the fidelity of the PCR-generated proinsulin analog gene itself. Plasmid DNA was sequenced using a TaqTrack kit and deaza-nucleotides (Promega, Madison, Wis.) plus a primer that hybridized within the pro region of XPR2 to generate sequence information across the XPR2 pro-proinsulin junction and through the proinsulin gene. The sequence of this primer is TACACGGATGGATCTGG (SEQUENCE I.D. NO: 16). One such proinsulin analog expression vector was named pXPRURAINS.

Plasmid pXPRURAINS was then digested with MluI (a unique site within the XPR2 promoter) and SacI (a unique site at the 3' end of the proinsulin analog gene), and a 1.7 kb DNA fragment was electrophoretically gel isolated. The 1.7 kb DNA fragment was ligated to a 7.3 kb DNA fragment generated by digesting pXPRLEUcas with MluI and SacII. Plasmid pXPRLEUcas, also designated pNB268, has been deposited in the American Type Tissue Collection as described hereinabove and has been assigned deposit number ATCC 69355. The ligation mix was transformed into *E. coli* DH5-α and transformants were plated on LB containing 100 µg/ml ampicillin. DNA was prepared from several transformants and digested with HindIII to identify a correct plasmid (named pXPRLEUINS) as depicted in FIG. 4.

Plasmid pXPRLEUINS was then digested with SacII, treated with Klenow fragment to generate blunt ends and religated. This destroyed the SacII site at the 3' end of the proinsulin analog gene so that the SacII site within the rDNA fragment of pNB650 would be unique, and digestion at this site could be used to target integration of the multiple integrative expression vector to rDNA loci. The ligation mix was transformed into *E. coli* DH5-α and transformants were plated on LB containing 100 µ/ml ampicillin. Transformant DNA was prepared and digested with SacII. A correct plasmid was identified which no longer was linearized upon digestion with SacII. That plasmid was named pXPRLEUINS(-SacII). Plasmid PXPRLEUINS(-SacII) was then digested with EcoRI to remove the wild-type LEU2 gene, and the 7.4 kb vector fragment was ligated to a 2.2 kb EcoRI DNA fragment containing the defective LEU2 ((d) LEU) gene isolated from pNB276. The ligation mix was transformed into *E. coli* DH5-α, and transformants were plated on LB containing 100 µg/ml ampicillin. The correct plasmid was identified by restriction digestion with EcoRI, which released a single 2.2 kb DNA fragment containing the (d)LEU gene instead of the wild-type 1.6 and 0.9 kb EcoRI DNA fragments. The correct plasmid was designated pXPR (d)LEUINS. This plasmid was then linearized by partial digestion with HindIII, as described hereinabove, dephosphorylated by treatment with calf intestinal phosphatase and ligated to the 2.8 kb HindIII DNA fragment containing rDNA sequences from pNB650 described above. The ligation mix was transformed into *E. coli* DH5-α and transformants were plated on LB containing 100 µg/ml ampicillin. The correct plasmid, in which rDNA sequences had been ligated at the HindIII site upstream of the XPR2 promoter, was identified by restriction digestion with EcoRI, which released fragments of 4.9, 5.4, and 2.4 kb. This plasmid was designated pMIVINS.

8. CONSTRUCTION OF PROINSULIN ANALOG EXPRESSING MULTIPLE INTEGRATION VECTOR TRANSFORMANTS OF *Y. lipolytica*.

Plasmid pMIVINS was digested with SacII to target it to the rDNA locus and transformed into *Y. lipolytica* strain NBL464 (ATCC 74234). Transformants were obtained after 48 hours at 29° C. on complete minimal medium minus leucine. DNA was obtained from two sets of transformants in separate experiments designated 1 and 2 in Table IV below. The genomic DNA was digested with HindIII and EcoRI (experiment 1) or with HindIII (experiment 2), fragments were separated electrophoretically on an 0.7% agarose gel and blotted to Hybond N membrane. The membrane was probed with a labeled 0.8 kb PstI-MluI DNA fragment isolated from the promoter region of XPR2. This probe hybridized to a 3.7 kb HindIII DNA fragment from the genomic copy of XPR2 (from either the HindIII-EcoRI digest or the HindIII digest) as well as to a 2.8 kb HindIII DNA fragment from pMIVINS (from either the HindIII-EcoRI digest or the HindIII digest). The blots were scanned using a BetaScope 603 Blot Analyzer as previously described to determine the number of copies of pMIVINS integrated into each transformant strain. Control transformants (NBL449 and NBL451), not necessary for practice of this invention and which were prepared as described below, were also analyzed by the same procedure.

Control transformants NBL449 and NBL451 were prepared as follows. Plasmid pXPRURAINS was digested with XhoI to target integration thereof into the URA3 locus, and transformed into Y. lipolytica strain NBL369 (MATB, bio-6::BIO(pBR322),leu2-40, xpr2-1002, ura 3Δ). Transformants were plated on complete minimal medium uracil to identify Ura$^+$ transformants. Then, pXPRLEUINS was digested with XhoI to target integration thereof into the LEU2 locus, and used to separately transform Y. lipolytica strain NBL369 and a Ura$^+$ transformant obtained as described immediately above. Transformants from each transformation were plated on complete minimal medium minus leucine or minus uracil and leucine to identify Leu$^+$ and Leu$^+$Ura$^+$ transformants, respectively. A Leu$^+$ transformant containing one copy of pXPRLEUINS was named NBL449. A Leu$^+$Ura$^+$ transformant containing one copy of pXPRURAINS and one copy of pXPRLEUINS (i.e., two copies of the proinsulin analog coding sequence) was named NBL451. Table IV, below, presents the copy number of the transformant strains so tested as well control transformants NBL449 and NBL451.

TABLE IV

| Transformant | Copy Number |
| --- | --- |
| 1-1 | 5 |
| 1-2 | 3 |
| 1-3 | 4 |
| 1-4 | 4 |
| 1-5 | 5 |
| 1-6 | 4 |
| 1-7 | 3 |
| 1-8 | 3 |
| 1-9 | 3 |
| NBL449 | 1 |
| NBL451 | 2 |
| 2-1 | 4 |
| 2-2 | 4 |
| 2-3 | 5 |
| 2-4 | 5 |
| 2-5 | 3 |
| 2-6 | 4 |
| 2-7 | 2 |
| 2-8 | 2 |
| 2-9 | 5 |
| 2-10 | 4 |
| 2-11 | 2 |
| 2-12 | 4 |
| 2-13 | 4 |
| 2-14 | 5 |
| 2-15 | 2 |
| 2-16 | 5 |

TABLE IV-continued

| Transformant | Copy Number |
| --- | --- |
| NBL449 | 1 |
| NBL451 | 2 |

Radioimmunoassay (RIA) was used to determine the relative amount of proinsulin analog related material secreted by the Y. lipolytica transformants comprising multiple copies of pMIVINS. The above-described transformant strains were grown in Medium A (5% Bacto-peptone, 1% glucose, 0.1% yeast extract) for 48 hours and then the supernatants were collected. Then, C-peptide RIAs, which measure free C-peptide of insulin, were conducted using a commercially available kit (Incstar Corp., Stillwater, N. Mex.). The C-peptide antibody reactive material was found to increase with increasing copy number. The five copy transformant secreted about 4 to 4.5 times the amount of C-peptide related protein as did the single copy proinsulin expression strain.

9. CONSTRUCTION OF INSULINOTROPIN MULTIPLE INTEGRATIVE EXPRESSION VECTOR

A synthetic gene encoding insulinotropin was prepared according to the following scheme: SEQUENCE I.D. NOS. 17, 18, 19 and 20 having the following sequences:

CACGCCGAGGGCACCTTCACCTCCGACGTCTCCTC (SEQUENCE I.D. NO: 17);

CCGGGTGCGGCTCCCGTGGAAGTGGAG-GCTGCAGAGGAGGATGG (SEQUENCE I.D. NO: 18);

CTACCTGGAGGGACAGGCCGCCAAG-GAGTTCATCGCCTGGCTGGTCAAGG GACGAG-GATAGT (SEQUENCE I.D. NO: 19); and ACCTCCCTGTCCGGCGGTTCCTCAAG-TAGCGGACCGACCAGTTCC CTGCTCCTATCA-GATC (SEQUENCE I.D. NO: 20)

were obtained from Genosys Biotechnologies, Inc., The Woodlands, Tex. Then, SEQUENCE I.D. NOS: 17 and 18 were hybridized together by heating at 100° C. for 10 min. and cooling slowly to room temperature and SEQUENCE I.D. NOS: 19 and 20 were hybridized together under the same conditions. The resulting hybridized sequences were treated with polynucleotide kinase and ligated using T4 DNA ligase to yield a 100 bp fragment encoding insulinotropin and containing an ApaI sticky 5' end and an XbaI sticky 3' end. The fragment was then ligated into ApaI/XbaI digested plasmid pBluescript+KS (Stratagene Cloning Systems, LaJolla, Calif.) for use in sequence verification. A plasmid containing the verified coding sequence was designated pNB716. Once the sequence was verified, an initial expression vector (pNB747) was constructed as follows and as depicted schematically in FIG. 5.

Figure 5A:
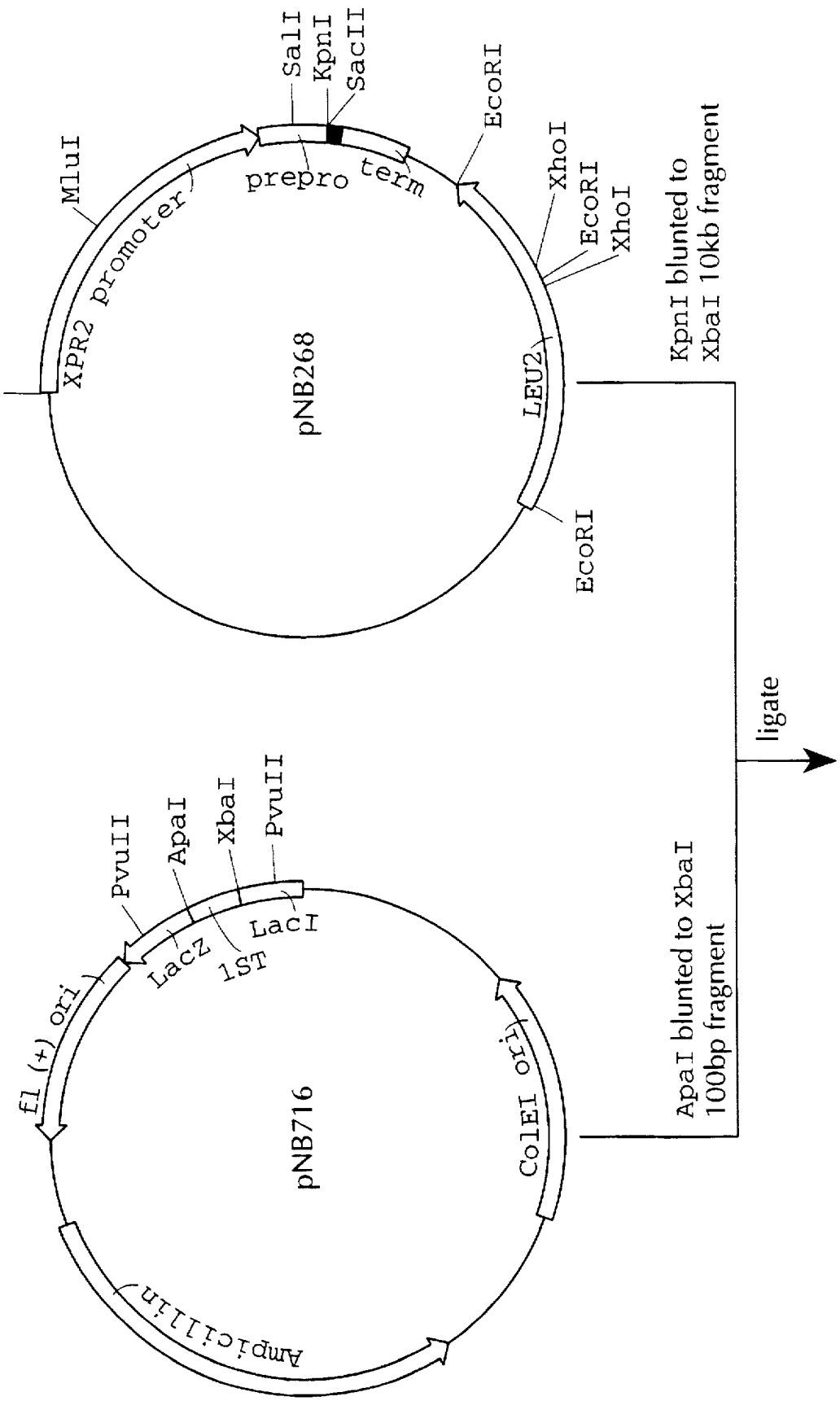
FIGS. 5A–5B are schematic representations of the construction of plasmid pNB747.
Figure 5B:
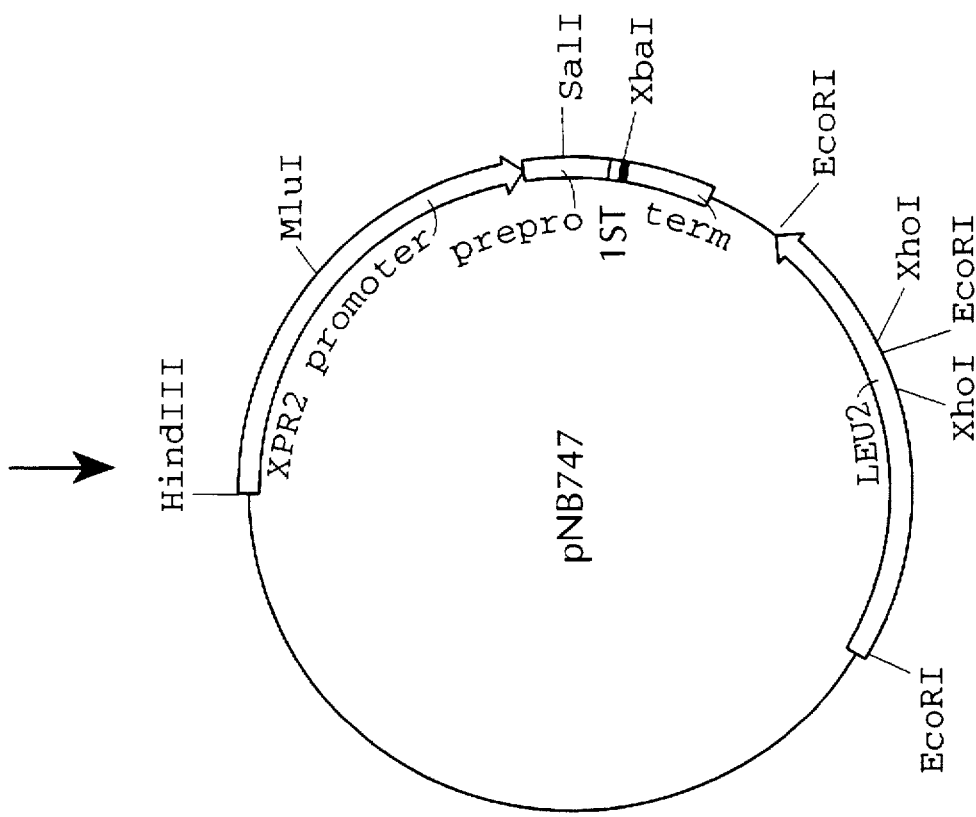

Plasmid pNB268 (ATCC 69355) DNA was digested with KpnI and the sticky ends were blunted using T4 DNA polymerase. The DNA was then digested with XbaI to receive the 3' end of the insulinotropin encoding fragment prepared as described above. The DNA of plasmid pNB716 containing the insulinotropin encoding sequence was digested with ApaI and the sticky ends were blunted with T4 DNA polymerase. The DNA was then digested with XbaI. The resulting 100 bp fragment was electrophoretically isolated on 2.0%, NuSieve agarose (FMC BioProducts, Rockland, Me.) gel and ligated to the KpnI digested, blunted and XbaI digested DNA of pNB268. The resulting ligation mix was used to transform *E. coli* DH5-α. Plasmids having the correct construction were identified by restriction enzyme analysis and the blunted junction region was sequenced to verify an in-frame fusion between the XPR2 prepro sequences and the insulinotropin encoding sequence. One such plasmid, pNB747, is shown in FIG. 5.

Plasmid pNB747 was digested with EcoRI to remove the wild-type LEU2 gene, and the 7.4 kb vector fragment was ligated to a 2.2 kb EcoRI DNA fragment containing the defective LEU2 ((d)LEU) gene isolated from pNB276. The ligation mix was transformed into *E. coli* DH5-α and transformants were plated on LB containing 100 μg/ml ampicillin. The correct plasmid was identified by restriction digestion with EcoRI, which released a single 2.2 kb DNA fragment containing the (d) LEU gene instead of the wild-type 1.6 and 0.9 kb EcoRI DNA fragments. The correct plasmid was designated pNB751.

Plasmid pNB751 was then digested with SacII, treated with Klenow fragment to generate blunt ends and religated. This destroyed the SacII site at the 3' end of the insulinotropin gene so that the SacII site within the rDNA fragment of pNB650 would be unique, and digestion at this site could be used to target integration of the multiple integrative expression vector to rDNA loci. The ligation mix was transformed into *E. coli* DH5-α and transformants were plated on LB containing 100 μ/ml ampicillin. Transformant DNA was prepared and digested with SacII. A correct plasmid was identified which no longer was linearized upon digestion with SacII. That plasmid was named pXPRLEUIST(-SacII). Plasmid pXPRLEUIST(-SacII) was then digested with EcoRI to remove the wild-type LEU2 gene, and the 7.4 kb vector fragment was ligated to a 2.2 kb EcoRI DNA fragment containing the defective LEU2 ((d) LEU) gene isolated from pNB276. The ligation mix was transformed into *E. coli* DH5-α, and transformants were plated on LB containing 100 μg/ml ampicillin. The correct plasmid was identified by restriction digestion with EcoRI, which released a single 2.2 kb DNA fragment containing the (d)LEU gene instead of the wild-type 1.6 and 0.9 kb EcoRI DNA fragments. The correct plasmid was designated pXPR(d)LEUIST. This plasmid was then linearized by partial digestion with HindIII, as described hereinabove, dephosphorylated by treatment with calf intestinal phosphatase and ligated to the 2.8 kb HindIII DNA fragment containing rDNA sequences from pNB650 described above. The ligation mix was transformed into *E. coli* DH5-α and transformants were plated on LB containing 100 μg/ml ampicillin. The correct plasmid, in which rDNA sequences had been ligated at the HindIII site upstream of the XPR2 promoter, was identified by restriction digestion with EcoRI, which released fragments of 4.9, 5.4, and 2.4 kb. This plasmid was designated pMIVIST.

10. CONSTRUCTION OF INSULINOTROPIN EXPRESSING MULTIPLE INTEGRATION VECTOR TRANSFORMANTS OF *Y. lipolytica*.

Plasmid pMIVIST was used to transform *Y. lipolytica* strain NBL464 (ATCC 74234) after having been digested with SacII. The resulting transformants obtained on complete minimal medium minus leucine contained multiple integrated vectors. Correlation between integrated copy number and the level of expression of insulinotropin was unclear.

---

What is claimed is:

1. A modified *Y. lipolytica* LEU2 non-wild type gene promoter selected from the group consisting of nucleotides 693 to 798 of SEQUENCE I.D. NO: 1, nucleotides 718 to 798 of SEQUENCE I.D. NO: 1, nucleotides 718 to 798 of SEQUENCE I.D. NO: 1 wherein nucleotide 724 is changed from A to G, nucleotides 718 to 798 of SEQUENCE I.D. NO: 1 wherein nucleotide 725 is changed from T to G, nucleotides 718 to 798 of SEQUENCE I.D. NO: 1 wherein nucleotide 722 is changed from A to G, nucleotides 745 to 798 of SEQUENCE I.D. NO: 1.

2. A modified *Y. lipolytica* LEU2 gene comprising the modified LEU2 gene promoter according to claim 1 functionally linked to a *Y. lipolytica* LEU2 structural gene coding sequence.

3. A vector comprising the modified *Y. lipolytica* LEU2 gene according to claim 2.

4. The vector according to claim 3 comprising a *Y. lipolytica* DNA sequence sufficient for integrative transformation of *Y. lipolytica* at a locus other than the LEU2 locus of *Y. lipolytica*.

5. The vector according to claim 4 wherein the *Y. lipolytica* DNA sequence sufficient for integrative transformation is a *Y. lipolytica* ribosomal DNA sequence.

6. An expression vector comprising the vector according to claim 5, a nucleotide sequence coding for a polypeptide and a promoter functional in *Y. lipolytica* operably linked to the nucleotide sequence coding for the polypeptide.

7. A *Y. lipolytica* transformant comprising the expression vector according to claim 6.

8. A method of producing a polypeptide which comprises fermenting the *Y. lipolytica* transformant according to claim 7 in an aqueous nutrient medium comprising assimilable sources of carbon, nitrogen and inorganic salts.

9. The expression vector according to claim 6 wherein the promoter functional in *Y. lipolytica* is the XPR2 promoter of *Y. lipolytica*.

10. The expression vector according to claim 9 which comprises the signal, pro1- or pro2-sequence of the XPR2 gene of *Y. lipolytica*, or a functional fragment or equivalent thereof, operably linked to the nucleotide sequence coding for the polypeptide.

11. The expression vector according to claim 10 wherein the polypeptide is a heterologous polypeptide.

12. The expression vector according to claim 11 wherein the heterologous polypeptide is prochymosin, proinsulin, insulinotropin or human TGF-β3.

13. A *Y. lipolytica* transformant comprising the expression vector according to claim 12.

14. A method of producing a polypeptide which comprises fermenting the *Y. lipolytica* transformant according to claim 13 in an aqueous nutrient medium comprising assimilable sources of carbon, nitrogen and inorganic salts.

15. A process of producing insulinotropin which comprises fermenting the *Y. lipolytica* transformant according to claim 13 in an aqueous nutrient medium comprising assimilable sources of carbon, nitrogen and inorganic salts.

16. A *Y. lipolytica* transformant comprising the expression vector according to claim 10.

17. A method of producing a polypeptide which comprises fermenting the *Y. lipolytica* transformant according to claim 16 in an aqueous nutrient medium comprising assimilable sources of carbon, nitrogen and inorganic salts.

18. A *Y. lipolytica* transformant comprising the expression vector according to claim 9.

19. A method of producing a polypeptide which comprises fermenting the *Y. lipolytica* transformant according to claim 18 in an aqueous nutrient medium comprising assimilable sources of carbon, nitrogen and inorganic salts.

20. An expression vector comprising the vector according to claim 4, a nucleotide sequence coding for a polypeptide and a promoter functional in *Y. lipolytica* operably linked to the nucleotide sequence coding for the polypeptide.

21. The expression vector according to claim 20 wherein the promoter functional in *Y. lipolytica* is the XPR2 promoter of *Y. lipolytica*.

22. The expression vector according to claim 10 which comprises the signal, pro1- or pro2-sequence of the XPR2 gene of *Y. lipolytica*, or a functional fragment or equivalent thereof, operably linked to the nucleotide sequence coding for the polypeptide.

23. The expression vector according to claim 22 wherein the polypeptide is a heterologous polypeptide.

24. The expression vector according to claim 23 wherein the heterologous polypeptide is prochymosin, proinsulin, insulinotropin or human TGF-β3.

25. A *Y. lipolytica* transformant comprising the expression vector according to claim 24.

26. A method of producing a polypeptide which comprises fermenting the *Y. lipolytica* transformant according to claim 25 in an aqueous nutrient medium comprising assimilable sources of carbon, nitrogen and inorganic salts.

27. A *Y. lipolytica* transformant comprising the expression vector according to claim 20.

28. A method of producing a polypeptide which comprises fermenting the *Y. lipolytica* transformant according to claim 27 in an aqueous nutrient medium comprising assimilable sources of carbon, nitrogen and inorganic salts.

29. A method of producing a *Y. lipolytica* transformant comprising multiple integrated expression vectors which method comprises:

(a) transforming a *Y. lipolytica* strain having a deletion of the LEU2 gene thereof with the expression vector according to claim 20 which has been linearized by cleaving the expression vector in the DNA sequence sufficient for integrative transformation; and (b) selecting for the best growing transformants on a medium which lacks leucine.

30. A *Y. lipolytica* transformant comprising the vector according to claim 3.

31. Plasmid pMIVINS.

32. A *Y. lipolytica* transformant comprising plasmid pMIVINS according to claim 31.

33. A method of producing A14trp proinsulin which comprises fermenting the *Y. lipolytica* transformant according to claim 32 in an aqueous nutrient medium comprising assimilable sources of carbon, nitrogen and inorganic salts.

34. Plasmid pMIVIST.

35. A *Y. lipolytica* transformant comprising plasmid pMIVIST according to claim 34.

36. A process of producing insulinotropin which comprises fermenting the *Y. lipolytica* transformant according to claim 35 in an aqueous nutrient medium comprising assimilable sources of carbon, nitrogen and inorganic salts.

37. A method of producing a modified *Y. lipolytica* LEU2 promoter which method comprises:

(a) producing a DNA sequence having a 5' end and a 3' end, having homology or substantial homology to a region of SEQUENCE I.D. NO: 1 and wherein said 5' end is within, but not co-terminus with the 5' end of the promoter region of SEQUENCE I.D. NO: 1;

(b) producing a vector comprising (i) a DNA sequence wherein the 3' end of the DNA sequence produced according to step (a) is joined to the 5' end of a DNA sequence comprising nucleotides of SEQUENCE I.D. NO: 1 such that the structural gene for LEU2 is formed and (ii) a sequence coding for a second *Y. lipolytica* structural gene;

(c) transforming a *Y. lipolytica* host having a deletion of the LEU2 gene and a mutation or deletion in the structural gene corresponding to said second structural gene with the vector produced according to step (b) which vector has been cleaved within the region coding for said second structural gene;

(d) selecting *Y. lipolytica* transformants on a medium containing leucine but requiring said second structural gene for growth; and (e) screening the *Y. lipolytica* transformants of step (d) for a transformant which grows poorly on a medium lacking leucine.

38. The method according to claim 37 wherein said second structural gene is URA3.

39. An isolated nucleotide sequence selected from the group consisting of

GCAGGATCCG AATTCTCTTC CACATAGCAC GGGC (SEQUENCE I.D. NO: 7),
GCAGGATCCG AATTCCGTAT ATATACAAGA GCGTTTGCC (SEQUENCE I.D. NO: 8),
GCAGGATCCG AATTCCGTAT GTATACAAGA GCGTTTGCC (SEQUENCE I.D. NO: 9),
GCAGGATCCG AATTCCGTAT AGATACAAGA GCGTTTGCC (SEQUENCE I.D. NO: 10),
GCAGGATCCG AATTCCGTGT ATATACAAGA GCGTTTGCC (SEQUENCE I.D. NO: 11),
GCAGGATCCG AATTCCCACA GATTTTCACT CC (SEQUENCE I.D. NO: 12).

40. Plasmid pNB258.
41. *E. coli* ATCC 69353.
42. Plasmid pNB650.
43. *E. coli* ATCC 69354.
44. Plasmid pNB268.
45. *E. coli* ATCC 69355.
46. *Y. lipolytica* ATCC 74234.
47. Plasmid pNB308.

* * * * *